US009445867B1

(12) United States Patent
Zarins et al.

(10) Patent No.: US 9,445,867 B1
(45) Date of Patent: *Sep. 20, 2016

(54) METHODS FOR RENAL NEUROMODULATION VIA CATHETERS HAVING EXPANDABLE TREATMENT MEMBERS

(71) Applicant: Medtronic Ardian Luxembourg S.a.r.l., Luxembourg (LU)

(72) Inventors: Denise Zarins, Saratoga, CA (US); Hanson Gifford, III, Woodside, CA (US); Mark Deem, Mountain View, CA (US); Howard R. Levin, Teaneck, NJ (US); Mark Gelfand, New York, NY (US); Nicolas Zadno, Fremont, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/075,789

(22) Filed: Mar. 21, 2016

Related U.S. Application Data

(60) Continuation of application No. 14/611,651, filed on Feb. 2, 2015, now Pat. No. 9,327,122, which is a continuation of application No. 13/958,450, filed on Aug. 2, 2013, now abandoned, which is a (Continued)

(51) Int. Cl.
*A61B 18/12* (2006.01)
*A61B 18/14* (2006.01)

(Continued)

(52) U.S. Cl.
CPC .......... *A61B 18/1492* (2013.01); *A61B 18/12* (2013.01); *A61N 1/0551* (2013.01);

(Continued)

(58) Field of Classification Search
CPC .. A61N 1/0551; A61N 1/36117; A61N 7/00; A61N 2007/003; A61B 18/1492; A61B 2018/0022; A61B 2018/00267; A61B 2018/00404; A61B 2018/00434; A61B 2018/00511; A61B 2018/00613; A61B 2018/00577; A61B 2018/00642; A61B 2018/00648; A61B 2018/00791; A61B 2018/00875; A61B 18/12; A61B 18/04; A61B 18/16; A61B 2018/00351
See application file for complete search history.

(56) References Cited

U.S. PATENT DOCUMENTS 2,130,758 A  9/1938  Rose
2,276,995 A  3/1942  Milinowski (Continued)

FOREIGN PATENT DOCUMENTS

DE  3151180  8/1982
EP  0811395  12/1997

(Continued)

OTHER PUBLICATIONS

Page, I.H. "The Effect of Renal Denervation on Patients Suffering from Nephritis" J. Clin. Invest.Jul. 1935; 14(4): 443-458.*

(Continued)

*Primary Examiner* — Mark W Bockelman

(57) ABSTRACT

Methods and apparatus are provided for monopolar neuromodulation, e.g., via a pulsed electric field. Such monopolar neuromodulation may effectuate irreversible electroporation or electrofusion, necrosis and/or inducement of apoptosis, alteration of gene expression, action potential attenuation or blockade, changes in cytokine up-regulation and other conditions in target neural fibers. In some embodiments, monopolar neuromodulation is applied to neural fibers that contribute to renal function. In some embodiments, such monopolar neuromodulation is performed bilaterally.

25 Claims, 8 Drawing Sheets

Related U.S. Application Data continuation of application No. 13/371,285, filed on Feb. 10, 2012, now abandoned, which is a division of application No. 11/403,329, filed on Apr. 13, 2006, now Pat. No. 8,131,371, which is a continuation-in-part of application No. 11/129,765, filed on May 13, 2005, now Pat. No. 7,653,438, said application No. 11/403,329 is a continuation-in-part of application No. 10/408,665, filed on Apr. 8, 2003, now Pat. No. 7,162,303, said application No. 11/403,329 is a continuation-in-part of application No. 11/189,563, filed on Jul. 25, 2005, now Pat. No. 8,145,316, and a continuation-in-part of application No. 11/266,993, filed on Nov. 4, 2005, now Pat. No. 7,756,583, and a continuation-in-part of application No. 11/363,867, filed on Feb. 27, 2006, now Pat. No. 7,620,451.

(60) Provisional application No. 60/616,254, filed on Oct. 5, 2004, provisional application No. 60/624,793, filed on Nov. 2, 2004, provisional application No. 60/442,970, filed on Jan. 29, 2003, provisional application No. 60/415,575, filed on Oct. 3, 2002, provisional application No. 60/370,190, filed on Apr. 8, 2002, provisional application No. 60/813,589, filed on Dec. 29, 2005.

(51) Int. Cl.
*A61N 1/05* (2006.01)
*A61B 18/00* (2006.01)

(52) U.S. Cl.
CPC ............... *A61B2018/00267* (2013.01); *A61B 2018/00404* (2013.01); *A61B 2018/00434* (2013.01); *A61B 2018/00577* (2013.01); *A61B 2018/00613* (2013.01); *A61B 2018/00642* (2013.01); *A61B 2018/00648* (2013.01); *A61B 2018/00791* (2013.01)

(56) References Cited

U.S. PATENT DOCUMENTS

| | | |
|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens et al. |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler et al. |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage et al. |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus et al. |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault et al. |
| 4,674,482 A | 6/1987 | Waltonen et al. |
| 4,692,147 A | 9/1987 | Duggan |
| 4,709,698 A | 12/1987 | Johnston et al. |
| 4,715,852 A | 12/1987 | Reinicke et al. |
| 4,774,967 A | 10/1988 | Zanakis et al. |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,890,623 A | 1/1990 | Cook et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois et al. |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka et al. |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,300,068 A | 4/1994 | Rosar et al. |
| 5,304,120 A | 4/1994 | Crandell et al. |
| 5,304,206 A | 4/1994 | Baker, Jr. et al. |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,368,591 A | 11/1994 | Lennox et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,423,744 A | 6/1995 | Gencheff et al. |
| 5,425,364 A | 6/1995 | Imran |

(56) References Cited

U.S. PATENT DOCUMENTS

| | | |
|---|---|---|
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,791 A | 4/1996 | Sit'ko et al. |
| 5,531,778 A | 7/1996 | Maschino et al. |
| 5,540,730 A | 7/1996 | Terry, Jr. et al. |
| 5,540,734 A | 7/1996 | Zabara |
| 5,553,611 A | 9/1996 | Budd et al. |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens et al. |
| 5,584,863 A | 12/1996 | Rauch et al. |
| 5,588,964 A | 12/1996 | Imran et al. |
| 5,589,192 A | 12/1996 | Okabe et al. |
| 5,599,345 A | 2/1997 | Edwards et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,672,174 A | 9/1997 | Gough et al. |
| 5,688,266 A | 11/1997 | Edwards et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,722,401 A | 3/1998 | Pietroski et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,306 A | 9/1998 | Shapland et al. |
| 5,810,802 A | 9/1998 | Panescu et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,860,974 A | 1/1999 | Abele |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu et al. |
| 5,893,885 A | 4/1999 | Webster |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,954,719 A | 9/1999 | Chen et al. |
| 5,983,131 A | 11/1999 | Weaver et al. |
| 5,983,141 A | 11/1999 | Sluijter et al. |
| 6,004,269 A | 12/1999 | Crowley et al. |
| 6,006,134 A | 12/1999 | Hill et al. |
| 6,009,877 A | 1/2000 | Edwards |
| 6,010,613 A | 1/2000 | Walters et al. |
| 6,024,740 A | 2/2000 | Lesh |
| 6,026,326 A | 2/2000 | Bardy |
| 6,036,687 A | 3/2000 | Laufer et al. |
| 6,041,252 A | 3/2000 | Walker et al. |
| 6,051,017 A | 4/2000 | Loeb et al. |
| 6,058,328 A | 5/2000 | Levine et al. |
| 6,058,331 A | 5/2000 | King |
| 6,066,134 A | 5/2000 | Eggers et al. |
| 6,073,048 A | 6/2000 | Kieval et al. |
| 6,077,227 A | 6/2000 | Miesel et al. |
| 6,086,527 A | 7/2000 | Talpade |
| 6,091,995 A | 7/2000 | Ingle et al. |
| 6,117,101 A | 9/2000 | Diederich et al. |
| 6,122,548 A | 9/2000 | Starkebaum et al. |
| 6,123,718 A | 9/2000 | Tu et al. |
| 6,135,999 A | 10/2000 | Fanton et al. |
| 6,146,380 A | 11/2000 | Racz et al. |
| 6,149,620 A | 11/2000 | Baker et al. |
| 6,161,048 A | 12/2000 | Sluijter et al. |
| 6,171,306 B1 | 1/2001 | Swanson et al. |
| 6,178,349 B1 | 1/2001 | Kieval |
| 6,190,353 B1 | 2/2001 | Makower et al. |
| 6,192,889 B1 | 2/2001 | Morrish |
| 6,205,361 B1 | 3/2001 | Kuzma et al. |
| 6,208,894 B1 | 3/2001 | Schulman et al. |
| 6,214,032 B1 | 4/2001 | Loeb et al. |
| 6,219,577 B1 | 4/2001 | Brown, III et al. |
| 6,224,592 B1 | 5/2001 | Eggers et al. |
| 6,238,702 B1 | 5/2001 | Berde et al. |
| 6,245,026 B1 | 6/2001 | Campbell et al. |
| 6,246,912 B1 | 6/2001 | Sluijter et al. |
| 6,251,130 B1 | 6/2001 | Dobak, III et al. |
| 6,254,598 B1 | 7/2001 | Edwards et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,272,377 B1 | 8/2001 | Sweeney et al. |
| 6,272,383 B1 | 8/2001 | Grey et al. |
| 6,273,886 B1 | 8/2001 | Edwards et al. |
| 6,280,377 B1 | 8/2001 | Talpade |
| 6,287,304 B1 | 9/2001 | Eggers et al. |
| 6,287,608 B1 | 9/2001 | Levin et al. |
| 6,292,695 B1 | 9/2001 | Webster, Jr. et al. |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,366,808 B1 | 4/2002 | Schroeppel et al. |
| 6,366,815 B1 | 4/2002 | Haugland et al. |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,438,423 B1 | 8/2002 | Rezai et al. |

(56) References Cited

U.S. PATENT DOCUMENTS

| | | |
|---|---|---|
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,488,679 B1 | 12/2002 | Swanson et al. |
| 6,506,189 B1 | 1/2003 | Rittman, III et al. |
| 6,508,774 B1 | 1/2003 | Acker et al. |
| 6,514,226 B1 | 2/2003 | Levin et al. |
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,542,781 B1 | 4/2003 | Koblish et al. |
| 6,564,096 B2 | 5/2003 | Mest |
| 6,571,127 B1 | 5/2003 | Ben-Haim et al. |
| 6,592,567 B1 | 7/2003 | Levin et al. |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni |
| 6,605,084 B2 | 8/2003 | Acker et al. |
| 6,613,045 B1 | 9/2003 | Laufer et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,635,054 B2 | 10/2003 | Fjield et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,690,971 B2 | 2/2004 | Schauerte et al. |
| 6,692,738 B2 | 2/2004 | MacLaughlin et al. |
| 6,697,670 B2 | 2/2004 | Chomenky et al. |
| 6,711,444 B2 | 3/2004 | Koblish |
| 6,718,208 B2 | 4/2004 | Hill et al. |
| 6,735,471 B2 | 5/2004 | Hill et al. |
| 6,738,663 B2 | 5/2004 | Schroeppel et al. |
| 6,749,598 B1 | 6/2004 | Keren et al. |
| 6,752,805 B2 | 6/2004 | Maguire et al. |
| 6,786,904 B2 | 9/2004 | Doscher et al. |
| 6,795,728 B2 | 9/2004 | Chornenky et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,869,431 B2 | 3/2005 | Maguire et al. |
| 6,885,888 B2 | 4/2005 | Rezai |
| 6,916,656 B2 | 7/2005 | Walters et al. |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,958,060 B2 | 10/2005 | Mathiesen et al. |
| 6,969,388 B2 | 11/2005 | Goldman et al. |
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,155,284 B1 | 12/2006 | Whitehurst et al. |
| 7,162,303 B2 | 1/2007 | Levin et al. |
| 7,191,015 B2 | 3/2007 | Lamson et al. |
| 7,373,204 B2 | 5/2008 | Gelfand et al. |
| 7,444,183 B2 | 10/2008 | Knudson et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,756,583 B2 | 7/2010 | Demarais et al. |
| 8,131,371 B2 | 3/2012 | Demarais et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0087208 A1 | 7/2002 | Koblish et al. |
| 2002/0107515 A1 | 8/2002 | Edwards et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0139379 A1 | 10/2002 | Edwards et al. |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050635 A1 | 3/2003 | Truckai et al. |
| 2003/0050681 A1 | 3/2003 | Pianca et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0195507 A1 | 10/2003 | Stewart et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0233099 A1 | 12/2003 | Danaek et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |

(56) References Cited

U.S. PATENT DOCUMENTS

| | | |
|---|---|---|
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0167509 A1 | 8/2004 | Taimisto |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0085054 A1 | 4/2006 | Zikorus et al. |
| 2006/0089674 A1 | 4/2006 | Walters et al. |
| 2006/0095029 A1 | 5/2006 | Young et al. |
| 2006/0100618 A1 | 5/2006 | Chan et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0288070 A1 | 12/2007 | Libbus et al. |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0091255 A1 | 4/2008 | Caparso et al. |
| 2008/0140150 A1 | 6/2008 | Zhou et al. |
| 2008/0213331 A1 | 9/2008 | Gelfand et al. |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2010/0010567 A1 | 1/2010 | Deem et al. |
| 2010/0057150 A1 | 3/2010 | Demarais et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2011/0060324 A1 | 3/2011 | Wu et al. |
| 2011/0112400 A1 | 5/2011 | Emery et al. |
| 2011/0137298 A1 | 6/2011 | Nguyen et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2012/0143181 A1 | 6/2012 | Demarais et al. |

FOREIGN PATENT DOCUMENTS

| | | |
|---|---|---|
| EP | 2092957 | 8/2009 |
| WO | WO-85/01213 | 3/1985 |
| WO | WO-91/04725 | 4/1991 |
| WO | WO-9220291 | 11/1992 |
| WO | WO-93/02740 | 2/1993 |
| WO | WO-93/07803 | 4/1993 |
| WO | WO-94/00188 | 1/1994 |

(56) References Cited

FOREIGN PATENT DOCUMENTS

| | | |
|---|---|---|
| WO | WO-9407446 | 4/1994 |
| WO | WO-94/11057 | 5/1994 |
| WO | WO-95/25472 | 9/1995 |
| WO | WO-9531142 | 11/1995 |
| WO | WO 95/33514 | 12/1995 |
| WO | WO-96/00039 | 1/1996 |
| WO | WO-96/04957 | 2/1996 |
| WO | WO-96/11723 | 4/1996 |
| WO | WO-97/13463 | 4/1997 |
| WO | WO-97/13550 | 4/1997 |
| WO | WO-9736548 | 10/1997 |
| WO | WO-97/49453 | 12/1997 |
| WO | WO-98/37926 | 9/1998 |
| WO | WO-98/42403 | 10/1998 |
| WO | WO-98/43700 | 10/1998 |
| WO | WO-98/43701 | 10/1998 |
| WO | WO-98/48888 | 11/1998 |
| WO | WO-99/33407 | 7/1999 |
| WO | WO-99/51286 | 10/1999 |
| WO | WO-99/52424 | 10/1999 |
| WO | WO-01/26729 | 4/2001 |
| WO | WO-0122897 | 4/2001 |
| WO | WO-0170114 | 9/2001 |
| WO | WO-02/09808 | 2/2002 |
| WO | WO-02/26314 | 4/2002 |
| WO | WO-02/053207 | 7/2002 |
| WO | WO-02/070039 | 9/2002 |
| WO | WO-02/070047 | 9/2002 |
| WO | WO-02/085448 | 10/2002 |
| WO | WO-02085192 | 10/2002 |
| WO | WO-03/018108 | 3/2003 |
| WO | WO-03022167 | 3/2003 |
| WO | WO-03/028802 | 4/2003 |
| WO | WO-03/063692 | 8/2003 |
| WO | WO 03/071140 | 8/2003 |
| WO | WO-03/076008 | 9/2003 |
| WO | WO-03/082080 | 10/2003 |
| WO | WO-03/082403 | 10/2003 |
| WO | WO-2004/026370 | 4/2004 |
| WO | WO-2004/026371 | 4/2004 |
| WO | WO-2004/026374 | 4/2004 |
| WO | WO-2004/030718 | 4/2004 |
| WO | WO-2004/032791 | 4/2004 |
| WO | WO-2004/107965 | 12/2004 |
| WO | WO-2005/014100 | 2/2005 |
| WO | WO-2005/016165 | 2/2005 |
| WO | WO-2005/032646 | 4/2005 |
| WO | WO-2005030072 | 4/2005 |
| WO | WO-2005041748 | 5/2005 |
| WO | WO-2005/065284 | 7/2005 |
| WO | WO-2005/084389 | 9/2005 |
| WO | WO-2005/097256 | 10/2005 |
| WO | WO-2005/110528 | 11/2005 |
| WO | WO-2005/123183 | 12/2005 |
| WO | WO-2006/007048 | 1/2006 |
| WO | WO-2006/018528 | 2/2006 |
| WO | WO-2006/022790 | 3/2006 |
| WO | WO-2006/031899 | 3/2006 |
| WO | WO-2006041847 | 4/2006 |
| WO | WO-2006041881 | 4/2006 |
| WO | WO-2006105121 | 10/2006 |
| WO | WO-2007008954 | 1/2007 |
| WO | WO-2007035537 | 3/2007 |
| WO | WO-2007078997 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008049084 | 4/2008 |
| WO | WO-2008061150 | 5/2008 |
| WO | WO-2008061152 | 5/2008 |
| WO | WO-2008070413 | 6/2008 |
| WO | WO-2010078175 | 7/2010 |

OTHER PUBLICATIONS

European Search Report for European Application No. 13159256, Date Mailed: Oct. 17, 2013, 6 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news--latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.

(56) References Cited

OTHER PUBLICATIONS

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dubuc, M., et al., "Feasibility of cardiac cryoablation using a transvenous steerable electrode catheter." J Interv Cardiac Electrophysiol, 2:285-292 (1998).

Final Office Action; U.S. Appl. No. 12/827,700; Mailed on Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." *Am. J. Roentgenol*,174: 1592-1594 (2000).

Han, Y.-M, et al., "Renal artery embolization with diluted hot contrast medium: An experimental study." J Vasc Intery Radiol, 12: 862-868 (2001).

Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S. J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D. L., et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Stella, A., et al., "Effects of reversible renal denervation on haemodynamic and excretory functions on the ipsilateral and contralateral kidney in the cat." Hypertension, 4:181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J. F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

(56) References Cited

OTHER PUBLICATIONS

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Schneider, Peter A., "Endovascular Skills—Guidewire and Catheter Skills for Endovascular Surgery," Second Edition Revised and Expanded, 10 pages, (2003).
Kandarpa, Krishna et al., "Handbook of Interventional Radiologic Procedures", Third Edition, pp. 194-210 (2002).
ThermoCool Irrigated Catheter and Integrated Ablation System, Biosense Webster (2006), 6 pages.
Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Oz, Mehmet, Pressure Relief, Time, Jan. 9, 2012, 2 pages. <www.time.come/time/printout/0,8816,2103278,00.html>.
Prochnau, Dirk et al., Catheter-based renal denervation for drug-resistant hypertension by using a standard electrophysiology catheter; Euro Intervention 2012, vol. 7, pp. 1077-1080.
Papademetriou, Vasilios, Renal Sympathetic Denervation for the Treatment of Difficult-to-Control or Resistant Hypertension, Int. Journal of Hypertension, 2011, 8 pages.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 60/852,787, filed Oct. 18, 2006, 105 pages.
Pieper et al., "Design and Implementation of a New Computerized System for Intraoperative Cardiac Mapping." Journal of Applied Physiology, 1991, vol. 71, No. 4, pp. 1529-1539.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
U.S. Appl. No. 60/813,589, filed Dec. 29, 2005, Demarais et al.
2003 European Society of Hypertension—European Society of Cardiology guidelines for the management of arterial hypertension, Guidelines Committee, Journal of Hypertension 2003, vol. 21, No. 6, pp. 1011-1053.
Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.
Abramov, G.S. et al., Alteration in sensory nerve function following electrical shock, Burns vol. 22, No. 8, 1996 Elsevier Science Ltd., pp. 602-606.
Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.
Advanced Neuromodulation Systems' Comparison Chart, Dec. 16, 2008, pp. 1.
Advances in the role of the sympathetic nervous system in cardiovascular medicine, 2001 SNS Report, No. 3, Springer, Published with an educational grant from Servier, pp. 1-8.
Aggarwal, A. et al., Regional sympathetic effects of low-dose clonidine in heart failure. Hypertension. 2003;41:553-7.
Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.
Ahadian, Farshad M., M.D., Pulsed Radiofrequency Neurotomy: Advances in Pain Medicine, Current Pain and Headache Reports 2004, vol. 8, 2004 Current Science Inc., pp. 34-40.
Alexander, B.T. et al., Renal denervation abolishes hypertension in low-birth-weight offspring from pregnant rats with reduced uterine perfusion, Hypertension, 2005; 45 (part 2): pp. 754-758.
Alford, J. Winslow, M.D. and Paul D. Fadale, M.D., Evaluation of Postoperative Bupivacaine Infusion for Pain Management After Anterior Cruciate Ligament Reconstruction, The Journal of

(56) References Cited

OTHER PUBLICATIONS

Arthroscopic and Related Surgery, vol. 19, No. 8, Oct. 2003 Arthroscopy Association of North America, pp. 855-861.
Allen, E.V., Sympathectomy for essential hypertension, Circulation, 1952, 6:131-140.
Amersham Health. Hypaque-Cysto, 2003, 6 pages.
Andrews, B.T. et al., The use of surgical sympathectomy in the treatment of chronic renal pain. Br J Urol. 1997; 80: 6-10.
Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.
Archer, Steffen et al., Cell Reactions to Dielectrophoretic Manipulation, Mar. 1, 1999, Biochemical and Biophysical Research Communications, 1999 Academic Press, pp. 687-698.
Arentz, T. et al., Incidence of pulmonary vein stenosis 2 years after radiofrequency catheter ablation of refractory atrial fibrillation. European Heart Journal. 2003. 24; pp. 963-969.
Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.
Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.
Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.
Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.
Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.
Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.
Badyal, D. K., H. Lata and A.P. Dadhich, Animal Models of Hypertension and Effect of Drugs, Aug. 19, 2003, Indian Journal of Pharmacology 2003, vol. 35, pp. 349-362.
Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.
Balazs, Tibor, Development of Tissue Resistance to Toxic Effects of Chemicals, Jan. 26, 1974, Toxicology, 2 (1974), Elsevier/North-Holland, Amsterdam, pp. 247-255.
Barajas, L. Innervation of the renal cortex. Fex Proc. 1978;37:1192-201.
Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.
Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.
Bassett, C. Andrew L. et al., Augmentation of Bone Repair by Inductively Coupled Electromagnetic Fields, May 3, 1974, Science, vol. 184, pp. 575-577.
Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.

Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.
Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.
Bello-Reuss, E. et al., Acute unilateral renal denervation in rats with extracellular volume expansion, Departments of Medicine and Physiology, University of North Carolina School of Medicine. F26-F32 Jul., 1975.
Bello-Reuss, E. et al., Effect of renal sympathetic nerve stimulation on proximal water and sodium reabsorption, J Clin Invest, 1976;57:1104-1107.
Bello-Reuss, E. et al., Effects of Acute Unilateral Renal Denervation in the Rat, J Clin Invest, 1975;56:208-217.
Berde, C. et al., Local Anesthetics, Anesthesia, Chapter 13, 5th addition, Churchill-Livingston, Philadelphia 2000, pp. 491-521.
Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.
Bhandari, A. and Ellias, M., Loin pain hematuria syndrome: Pain control with RFA to the Splanchanic plexus, The Pain Clinic, 2000, vol. 12, No. 4, pp. 323-327.
Bhatt, Deepak L. et al., Rhabdomyolysis Due to Pulsed Electric Fields, May 11, 1989, Plastic and Reconstructive Surgery Jul. 1990, pp. 1-11.
Bichet, D., et al., Renal intracortical blood flow and renin secretion after denervation by 6-hydroxydopamine. Can J Physiol Pharmacol. 1982;60:184-92.
Bigler, D. et al., Tachyphylaxis during postoperative epidural analgesia—new insights, Apr. 15, 1987, Letter to the Editor, Acta Anaesthesiol Scand. 1987, vol. 31, pp. 664-665.
Binder, Allan et al., Pulsed Electromagnetic Field Therapy of Persistent Rotator Cuff Tendinitis, The Lancet, Saturday Mar. 31, 1984, The Lancet Ltd., pp. 695-698.
Black, M.D., Henry R., Resistant Hypertension 2004, presentation at Rush University Medical Center, Jul. 15, 2004, 40 pages.
Blad, B., et al., An Electrical Impedance index to Assess Electroporation in Tissue, Tissue and Organ (Therapy), 2001, Oslo, www.bl.uk <http://www.bl.uk> British Library, pp. 31-34.
Blair, M. L. et al, Sympathetic activation cannot fully account for increased plasma renin levels during water deprivation, Sep. 23, 1996, Am. J. Physiol., vol. 272, 1997, the American Physiological Society 1997, pp. R1197-R1203.
Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.
Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005, 31 slides.
Bourge, R.C., Heart Failure Monitoring Devices: Rationale and Status 28 pages, Feb. 2001.
Braunwald, E., Heart Disease, A Textbook of Cardiovascular Medicine, 5th Ed., vol. 2, 1997, pp. 480-481, 824-825, 1184-1288 and 1923-1925, W.B. Saunders Company.
Bravo, E.L., et al., Renal denervation for resistant hypertension, American Journal of Kidney Diseases, 2009, 3 pgs.
Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. pp. 1318-1325. Dec. 2005.
Burkhoff, D., Interventional Device-Based Therapy for CHF Will Redefine Current Treatment Paradigms. Columbia University. 2004. 32 slides.
Burns, J. et al., Relationship between central sympathetic drive and magnetic resonance imaging-determined left ventricular mass in essential hypertension. Circulation. 2007;115:1999-2005.

(56) References Cited

OTHER PUBLICATIONS

Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.

Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.

Calaresu, F.R. et al., Haemodynamic Responses and Renin Release During Stimulation of Afferent Renal Nerves in the Cat, Aug. 12, 1975, J. Physiol. 1976, vol. 255, pp. 687-700.

Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.

Campese, V.M. et al., Renal afferent denervation prevents hypertension in rats with chronic renal failure. Hypertension. 1995;25:878-82.

Campese, V.M. et al., Renal Afferent Denervation Prevents the Progression of Renal Disease in the Renal Ablation Model of Chronic Renal Failure in the Rat, Am J Kidney Dis. 1995;26:861-5.

Campese, V.M., A new model of neurogenic hypertension caused by renal injury: pathophysiology and therapeutic implications, Clin Exp Nephrol (2003) 7: 167-171, Japanese Society of Nephrology 2003.

Campese, V.M., Neurogenic factors and hypertension in chronic renal failure, Journal of Nephrology, vol. 10, No. 4, 1997, Societa Italiana di Nefrologia, pp. 184-187.

Campese, V.M., Neurogenic factors and hypertension in renal disease. Kidney Int. 2000;57 Suppl 75:S2-3.

Canbaz, S. et al., Electrophysiological evaluation of phrenic nerve injury during cardiac surgery—a prospective, controlled clinical study. BioMed Central. 5 pgs. 2004.

Cardiac Glycosides, Heart Disease—A Textbook of Cardiovascular Medicine vol. 2, Edited by Eugene Braunwald, 5th Edition, 1997 WB Saunders Company, pp. 480-481.

Carls, G. et al., Electrical and magnetic stimulation of the intercostal nerves: a comparative study, Electromyogr, din. Neurophysiol. 1997, vol. 37, pp. 509-512.

Carlson, Scott H. and J. Michael Wyss, e-Hypertension—Opening New Vistas, Introductory Commentary, Hypertension 2000, vol. 35, American Heart Association, Inc. 2000, p. 538.

Carson, P., Device-based Treatment for Chronic Heart Failure: Electrical Modulation of Myocardial Contractility. Transcatheter Cardiovascular Therapeutics 2005, 21 slides.

Chang, Donald C., Cell poration and cell fusion using an oscillating electric field, Biophysical Journal, vol. 56, Oct. 1989, Biophysical Society, pp. 641-652.

Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.

Chin, J.L. et al., Renal autotransplantation for the loin pain-hematuria syndrome: long term follow up of 26 cases, J Urol, 1998, vol. 160, pp. 1232-1236.

Chiou, C.W. et al., Efferent Vagal Innervation of the Canine Atria and Sinus and Atrioventricular Nodes. Circulation. Jun. 1997. 95(11):2573-2584. Abstract only. 2 pgs.

Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.

Clinical Trials in Hypertension and Renal Diseases, Slide Source, www.hypertensiononline.org, 33 pages Aug. 13, 2001.

Conradi, E. and Ines Helen pp., Effects of Continous and Pulsed Microwave Irradiation on Distribution of Heat in the Gluteal Region of Minipigs, Scand J Rehab Med, vol. 21, 1989, pp. 59-62.

Converse, R.L., Jr. et al., Sympathetic Overactivity in Patients with Chronic Renal Failure, N Engl J Med. Dec. 31, 1992, vol. 327 (27), pp. 1912-1918.

Cosman, E.R., Jr. et al., Electric and Thermal Field Effects in Tissue Around Radiofrequency Electrodes, Pain Medicine, vol. 6, No. 6, 2005, American Academy of Pain Medicine, pp. 405-424.

Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.

Crawford, William H. et al., Pulsed Radio Frequency Therapy of Experimentally Induced Arthritis in Ponies, Dec. 18, 1989, Can. J. Vet. Res. 1991, vol. 55, pp. 76-85.

Curtis, J.J. et al., Surgical theray for persistent hypertension after renal transplantation, Transplantation, 1981, 31(2):125-128.

Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.

Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.

Dang, Nicholas C. et al., A Novel Approach to Increase Total Urine Output in Heart Failure: Renal Nerve Blockade, ACC 2005 poster; 1 page.

Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.

Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.

Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.

De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.

Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.

Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.

Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.

Dev, Nagendu B., Ph.D. et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.

Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.

Dibona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.

Dibona, Gerald F. and Susan Y. Jones, Dynamic Analysis of Renal Nerve Activity Responses to Baroreceptor Denervation in Hypertensive Rats, Sep. 19, 2000, Hypertension Apr. 2001, American Heart Association, Inc. 2001, pp. 1153-1163.

Dibona, Gerald F. and Ulla C. Kopp, Neural Control of Renal Function, Physiological Reviews, vol. 77, No. 1, Jan. 1997, the American Physiological Society 1997, pp. 75-197.

Dibona, Gerald F. and Ulla C. Kopp, Role of the Renal Sympathetic Nerves in Pathophysiological States, Neural Control of Renal Function, vol. 77, pp. 142-197 Jan. 1997.

(56) References Cited

OTHER PUBLICATIONS

Dibona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.
Dibona, Gerald F., L.L. Sawin, Effect of renal nerve stimulation on NaCl and H2O transport in Henle's loop of the rat,: 1982, American Physiological Society, F576-F580, 5 pgs.
Dibona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.
Dibona, Gerald F., Neural Control of the Kidney—Past, Present and Future, Nov. 4, 2002, Novartis Lecture, Hypertension 2003, 41 part 2, 2002 American Heart Association, Inc., pp. 621-624.
DiBona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.
DiBona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.
DiBona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.
DiBona, Gerald F., Sympathetic Nervous System and the Kidney in Hypertension, Current Opinion in Nephrology and Hypertension 2002, vol. 11, 2002 Lippincott Williams & Wilkins, pp. 197-200.
DiBona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.
DiBona, Gerald, LL Sawin, Effect of renal denervation on dynamic autoregulation of renal blood flow, Feb. 12, 2004, AmJ Physiol Renal Physiol 286, pp. F1209-F1218.
Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. pp. 845-852.
Dorros, Gerald, M.D., Renal Artery Stenting State of the Art, presentation, TCT, Washington D.C., Sep. 2003, 27 pages.
Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.
Dunn, Matthew D. et al., Laparoscopic Nephrectomy in Patients With End-Stage Renal Disease and Autosomal Dominant Polycystic Kidney Disease,Oct. 25, 1999, American Journal of Kidney Diseases, vol. 35, No. 4 Apr. 2000, National Kidney Foundation, Inc. 2000, pp. 720-725.
Durand, D.M., Electric Field Effects in Hyperexcitable Neural Tissue: A Review, Radiation Protection Dosimetry, vol. 106, No. 4, 2003 Nuclear Technology Publishing, pp. 325-331.
Effects of Renal Failure on the Cardiovascular System, 5th Edition Heart Disease, A Textbook of Cardiovascular Medicine, vol. 2, Edited by Eugene Braunwald, 1997, W.B. Saunders Company, pp. 1923-1925.
Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.
Electropermeabilization (Electroporation), Cyto Pulse Sciences, Inc., http://www.cytopulse.com/electroporation.html (last accessed Mar. 3, 2005), 3 pgs.
Electroporation based Technologies and Treatments, ESPE Newsletter No. 6, QLK 02002-2003, Jan. 2005, www.cliniporator.com, 4 pgs.
End-stage renal disease payment policies in traditional Medicare, Chapter 8, Report to the Congress: Medicare Payment Policy, Mar. 2001, Medpac, pp. 123-138.
Epidemiology of Renal Disease in Hypertension, slide presentation by hypertensiononline.org, 21 pages Mar. 30, 2001.
Erdine, Serap and Alev Arat-Ozkan, Resistant Hypertension, European Society of Hypertension Scientific Newsletter: Update on Hypertension Management 2003, vol. 4, No. 15, 2 pages.
Esler, M. et al., Mechanism of elevated plasma noradrenaline in the course of essential hypertension. J Cardiovasc Pharmacol. 1986;8:S39-43.
Esler, M. et al., Noradrenaline release and the pathophysiology of primary human hypertension. Am J Hypertens. 1989; 2:140S-146S.
Esler, M. et al., Sympathetic nerve biology in essential hypertension, Clin and Exp Pharmacology and Physiology, 2001, 28:986-989.
European Examination Report; European Patent Application No. 07799148.7; Applicant: Ardian, Inc.; Date of Mailing: Jan. 19, 2010, 4 pgs.
European Examination Report; European Patent Application No. 09156661.2; Applicant: Ardian, Inc.; Date of Mailing: Jan. 19, 2010, 6 pgs.
European Search Report; European Patent Application No. 05806045.0; Applicant: Ardian, Inc.; Date of Mailing: Sep. 22, 2009, 8 pgs.
European Search Report; European Patent Application No. 05811851.4; Applicant: Ardian, Inc.; Date of Mailing: Oct. 1, 2009, 7 pgs.
European Search Report; European Patent Application No. 06847926.0; Applicant: Ardian, Inc.; Date of Mailing: Feb. 10, 2010, 6 pgs.
European Search Report; European Patent Application No. 07757925.8; Applicant: Ardian, Inc.; Date of Mailing: Apr. 29, 2010, 9 pgs.
European Search Report; European Patent Application No. 07798341.9; Applicant: Ardian, Inc.; Date of Mailing Aug. 4, 2011; 6 pgs.
European Search Report; European Patent Application No. 07799148.7; Applicant: Ardian, Inc.; Date of Mailing: Jul. 23, 2009, 6 pgs.
European Search Report; European Patent Application No. 07868755.5; Applicant: Ardian, Inc.; Date of Mailing: Jul. 28, 2010, 7 pgs.
European Search Report; European Patent Application No. 09156661.2; Applicant: Ardian, Inc.; Date of Mailing: Jul. 23, 2009, 6 pgs.
European Search Report; European Patent Application No. 09167937.3; Applicant: Ardian, Inc.; Date of Mailing: Nov. 11, 2009, 6 pgs.
European Search Report; European Patent Application No. 09168202.1; Applicant: Ardian, Inc.; Date of Mailing: Nov. 11, 2009, 5 pgs.
European Search Report; European Patent Application No. 09168204.7; Applicant: Ardian, Inc.; Date of Mailing: Nov. 19, 2009, 6 pgs.
Evelyn, K.A. et al., Effect of thoracolumbar sympathectomy on the clinical course of primary (essential) hypertension, Am J Med, 1960;28:188-221.
Ex parte Quayle Office Action; U.S. Appl. No. 11/144,173; Mailed on May 28, 2009, 4 pgs.
Fact Book Fiscal Year 2003, National Institutes of Health National Heart, Lung, and Blood Institute, Feb. 2004, 197 pgs.
Fajardo, J. et al., Effect of chemical sympathectomy on renal hydroelectrolytic handling in dogs with chronic caval constriction. Clin Physiol Biochem. 1986;4:252-6.
Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.

(56) References Cited

OTHER PUBLICATIONS

Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.
Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.
Fields, Larry E. et al., The Burden of Adult Hypertension in the United States 1999 to 2000—A Rising Tide, May 18, 2004, American Heart Association 2004, Hypertension Oct. 2004, pp. 1-7.
Final Office Action; U.S. Appl. No. 11/233,814; Mailed on Jan. 29, 2009, 11 pgs.
Final Office Action; U.S. Appl. No. 11/266,993; Mailed on Jan. 8, 2010, 7 pgs.
Final Office Action; U.S. Appl. No. 11/363,867; Mailed on May 1, 2009, 8 pgs.
Final Office Action; U.S. Appl. No. 11/451,728; Mailed on Jan. 13, 2009, 7 pgs.
Final Office Action; U.S. Appl. No. 11/599,649; Mailed on Jan. 15, 2009, 10 pgs.
Final Office Action; U.S. Appl. No. 11/599,723; Mailed on Apr. 5, 2010, 17 pgs.
Final Office Action; U.S. Appl. No. 11/599,890; Mailed on Apr. 29, 2009, 9 pgs.
Fischell, Tim A. et al., Ultrasonic Energy: Effects on Vascular Function and Integrity, Circulation: Journal of the American Heart Association. 1991. 84;pp. 1783-1795.
Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.
Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.
Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.
Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.
Gattone II, Vincent H. et al., Contribution of Renal Innervation to Hypertension in Polycystic Kidney Disease in the Rat, University of Chicago Section of Urology, 16 pages, Mar. 17, 2008.
Gaylor, D.C. et al., Significance of Cell Size and Tissue Structure in Electrical Trauma, Jan. 26, 1988, J. theor. Biol. 1988, vol. 133, 1988 Academic Press Limited, pp. 223-237.
Gazdar, A.F. and G.J. Dammin, Neural degeneration and regeneration in human renal transplants, NEJM, Jul. 30, 1970, 283:222-244.
Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba <http:www.elsevier.com/locate/bba>.
Getts, R.T. et al., Regression of left ventricular hypertrophy after bilateral nephrectomy, Nephrol Dial Transplant, 2006, vol. 21, pp. 1089-1091.
Ghoname, El-sayed A. et al., Percutaneous electrical nerve stimulation: an alternative to TENS in the management of sciatica, Apr. 26, 1999, Pain 1999, vol. 83, 1999 International Association for the Study of Pain / Published by Elsevier Science B.V., pp. 193-199.
Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.
Goldberger, Jeffrey J. et al., New technique for vagal nerve stimulation, Jun. 2, 1999, Journal of Neuroscience Methods 91, 1999, Elsevier Science B.V. 1999, pp. 109-114.
Gorbunov, F.E. et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).
Gottschalk, C.W., Renal nerves and sodium excretion, Ann. Rev. Physiol., 1979, 41:229-240.
Greenwell, T.J. et al., The outcome of renal denervation for managing loin pain haematuria syndrome. BJU International, 2004; 4 pgs.
Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.
Guimaraes, Sarfim. Vascular Adrenoceptors: An Update. pp. 319-356, Jun. 1, 2001.
Haissaguerre, M. et al., Spontaneous initiation of atrial fibrillation by ectopic beats orginating in the pulmonary veins, New England Journal of Medicine, 1998, 339: 659-666.
Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.
Hammer, Leah W. Differential Inhibition of Functional Dilation of Small Arterioles by Indomethacin and Glibenclamide. Hypertension. Feb. 2001 Part II. pp. 599-603.
Hampers, C.L. et al., A hemodynamic evaluation of bilateral nephrectomy and hemodialysis in hypertensive man, Circulation. 1967;35:272-288.
Hamza, M.D., Mohamed A. et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.
Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.
Hansen, J.M. et al., The transplanted human kidney does not achieve functional reinnervation, Clin Science, 1994, vol. 87, pp. 13-20.
Hasking, G.J. et al., Norepinephrine spillover to plasma in patients with congestive heart failure: evidence of increased overall and cardiorenal sympathetic nervous activity. Circulation. 1986;73:615-21.
Hausberg, M. et al., Sympathetic nerve activity in end-stage renal disease, Circulation, 2002, 106: 1974-1979.
Heart Arrhythmia Heart and Vascular Health on Yahoo! Health. 13 pgs. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.
Heart Disease and Stroke Statistics—2004 Update, American Heart Association, American Stroke Association, Dallas, Texas, 2003 American Heart Association, 52 pgs.
Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.
Heuer, G.J., The surgical treatment of essential hypertension, Annals of Surgery, 1936; 104(4): 771-786.
Higuchi, Yoshinori, M.D., Ph.D. et al, Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.
Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.

(56) References Cited

OTHER PUBLICATIONS

Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.

Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997, Abstract, 2 pgs.

Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.

Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.

Horwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.

Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.

Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.

Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.

Hypertension and Renal Disease: Mechanisms, Slide Show by www.hypertensiononline.org, 22 pages Mar. 30, 2001.

Hypertension Incidence and Prevalence, Age-Specific Rates, by Gender, B.C., 2001/2002, Graph, Chronic Disease Management, May 2003, British Columbia Ministry of Health Services, 1 page.

Implantable Neurostimulation Systems, Medtronic Neurological, Jan. 18, 1999, 6 pages. http://medtronic.com/neuro/paintherapies/pain_treatment_ladder/pdf/implantable_brochure.pdf.

Implantable Pump—The Medtronic MiniMed 2007 Implantable Insulin Pump System, Medtronic MiniMed 2004, 4 pgs.

International Search Report and Written Opinion for PCT/US2009/069334; Applicant: Ardian, Inc.; Mailing Date: Mar. 1, 2010, 10 pgs.

International Search Report and Written Opinion, PCT/US05/35693, Mailed on Mar. 8, 2006, Applicant: Ardian, Inc., 29 pgs.

International Search Report and Written Opinion, PCT/US05/35757, Mailed on Dec. 27, 2006, Applicant: Ardian, Inc., 8 pgs.

International Search Report and Written Opinion, PCT/US06/36120, Mailed on Jun. 25, 2008, Applicant: Ardian, Inc., 10 pgs.

International Search Report and Written Opinion, PCT/US06/41889, Mailed on Oct. 20, 2008, Applicant: Ardian, Inc., 7 pgs.

International Search Report and Written Opinion, PCT/US06/48822, Mailed on Aug. 15, 2008, Applicant: Ardian, Inc., 12 pgs.

International Search Report and Written Opinion, PCT/US07/633222, Mailed on Mar. 3, 2008, Applicant: Ardian, Inc., 10 pgs.

International Search Report and Written Opinion, PCT/US07/63324, Mailed on Oct. 10, 2008, Applicant: Ardian, Inc., 10 pgs.

International Search Report and Written Opinion, PCT/US07/66539, Mailed on Jan. 28, 2008, Applicant: Ardian, Inc., 6 pgs.

International Search Report and Written Opinion, PCT/US07/70799, Mailed on Jul. 2, 2008, Applicant: Ardian, Inc., 7 pgs.

International Search Report and Written Opinion, PCT/US07/72396, Mailed on Aug. 27, 2008, Applicant: Ardian, Inc., 9 pgs.

International Search Report and Written Opinion, PCT/US07/84701, Mailed on Aug. 21, 2008, Applicant: Ardian, Inc., 11 pgs.

International Search Report and Written Opinion, PCT/US07/84705, Mailed on Jul. 28, 2008, Applicant: Ardian, Inc., 12 pgs.

International Search Report and Written Opinion, PCT/US07/84708, Mailed on Aug. 11, 2008, Applicant: Ardian, Inc., 9 pgs.

International Search Report, PCT/US02/0039, Mailed Sep. 11, 2002, Applicant: Advanced Neuromodulation Systems, Inc.

International Search Report, PCT/US02/25712, Mailed on Apr. 23, 2003, Applicant: Cyberonics, Inc.

International Search Report, PCT/US03/08014, Mailed on Sep. 23, 2003, Applicant: The General Hospital Corporation.

International Search Report, PCT/US03/09764, Mailed on Oct. 28, 2003, Applicant: CVRX, Inc.

International Search Report, PCT/US04/38498, Mailed Feb. 18, 2005, Applicant: G & L Consulting, LLC, 4 pgs.

Introduction to Autonomic Pharmacology, Chapter 3, Part 2 Autonomic Pharmacology, pp. 18-26, May 24, 2002.

Isovue: Data Sheet. Regional Health Limited. 8 pgs. Mar. 11, 2003.

Israili, Z.H., Clinical pharmacokinetics of angiotensin II (AT) receptor blockers in hypertension, Journal of Human Hypertension, 2000, Macmillan Publishers Ltd., vol. 14, pp. S73-S86.

Janda, J., Impact of the electrical stimulation apparatus rebox on the course of ischemic renal damage in rats, British Library—The world's knowledge pp. 252-254 (translated and untranslated versions) 1996.

Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.

Jia, Jianping et al., Cold injury to nerves is not due to ischaemia alone, Brain. 121;pp. 989-1001. 1998.

Jia, Jianping et al.., The pathogenesis of non-freezing cold nerve injury: Observations in the rat, Brain. 120; pp. 631-646. 1997.

Jin, Yuanzhe et al., Pulmonary Vein Stenosis and Remodeling After Electrical Isolation for Treatment of Atrial Fibrillation: Short- and Medium-Term Follow-Up, PACE, vol. 27., Oct. 2004, pp. 1362-1370.

Johansson, Bjorn, Electrical Membrane Breakdown, A Possible Mediator of the Actions of Electroconvulsive Therapy, Medical Hypotheses 1987, vol. 24, Longman Group UK Ltd 1987, pp. 313-324.

Joles, J.A. et al., Causes and Consequences of Increased Sympathetic Activity in Renal Disease. Hypertension. 2004;43:699-706.

Jorgensen, William A. et al., Electrochemical Therapy of Pelvic Pain: Effects of Pulsed Electromagnetic Fields (PEMF) on Tissue Trauma, Eur J Surg 1994, Suppl 574, vol. 160, 1994 Scandinavian University Press, pp. 83-86.

Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, pp. 052901-1-052901-4.

Joshi, R. P. et al., Improved energy model for membrane electroporation in biological cells subjected to electrical pulses, Apr. 9, 2002, Physical Review E, vol. 65, 041920-1, 2002 The American Physical Society, 8 pages.

Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.

Joye, James D.et al., In Vivo Study of Endovascular Cryotherapy for the Prevention of Restenosis, 4 pages, 2003.

Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.

Kassab, S. et al., Renal denervation attenuates the sodium retention and hypertension associated with obesity, Hypertension, 1995, 25:893-897.

Katholi, R.E. et al., Importance of the renal nerves in established two-kidney, one clip Goldblatt hypertension, Hypertension, 1982, 4 (suppl II): II-166-II-174.

(56) References Cited

OTHER PUBLICATIONS

Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.
Katholi, Richard E., Renal nerves in the pathogenesis of hypertension in experimental animals and humans, Am. J. Physiol. vol. 245, 1983, the American Physiological Society 1983, pp. F1-F14.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+] in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by The American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha1- and alpha2-adrenoceptors on renal sensory nerve fibers. Am J Physiol Regul Integr Comp Physiol. 2007;293:R1561-72.
Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.
Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.
Kumagai, K. et al. New Approach to Pulmonary Vein Isolation for Atrial Fibrillation Using a Multielectrode Basket Catheter. Circulation Journal. 2006;70:88-93.
Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.
Lavie, Peretz, Ph.D. and Victor Hoffstein, M.D., Sleep Apnea Syndrome: A Possible Contributing Factor to Resistant Hypertension, Jun. 2001, Sleep 2001, vol. 24, No. 6, pp. 721-725.
Le Noble, J.L. et al., Pharmacological evidence for rapid destruction of efferent renal nerves in rats by intrarenal infusion of 6-hydroxydopamine. J Hypertens Suppl. 1985;3:S137-40.
Lee, Michael A. (editor). SPORTSMed. Connecticut State Medical Society Committee on the Medical Aspects of Sports. Fall/Winter 2005. 10 pgs.
Lee, Raphael C. et al., Biophysical Injury Mechanisms in Electronic Shock Trauma, Annu. Rev. Biomed. Eng., 2000, vol. 2, Copyright © 2000 by Annual Reviews, pp. 477-509.
Lee, Raphael C. et al., Clinical Sequelae Manifested in Electrical Shock Survivors, Presentation by the Electrical Trauma Research Program, The University of Chicago, 37 pages Dec. 24, 2004.
Lee, Raphael C. et al., Membrane Biology and Biophysics, Chapter 25, Surgical Research, 2001 Academic Press, pp. 297-305.
Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.
Lenoble, L.M. et al., Selective efferent chemical sympathectomy of rat kidneys. Am J Physiol. 1985;249:R496-501.
Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.
Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.
Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.
Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.
Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.
Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.
Lohmeier, Thomas E., et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.
Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.
Lohmeier, Thomas E., Interactions Between Angiotensin II and Baroreflexes in Long-Term Regulation of Renal Sympathetic Nerve Activity, Circulation Research, Jun. 27, 2003, American Heart Association, Inc.2003, pp. 1282-1284.
Luff, S.E. et al., Two types of sympathetic axon innervating the juxtaglomerular arterioles of the rabbit and rat kidney differ structurally from those supplying other arteries, May 1, 1991, Journal of Neurocytology 1991, vol. 20, 1991 Chapman and Hall Ltd., pp. 781-795.
Luippold, G. et al., Chronic renal denervation prevents glomerular hyperfiltration in diabetic rats, Nephrol Dial Transplant (2004) 19:342-347.
Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.
Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.
Malpas, Simon C., What sets the long-term level of sympathetic nerve activity: is there a role for arterial baroreceptors?, Invited

(56) References Cited

OTHER PUBLICATIONS

Review, Am J Physiol Regul Integr Comp Physiol 2004, vol. 286, 2004 the American Physiological Society, pp. R1-R12.
Mancia, G., Grassi, G., Giannattasio, C., Seravalle, G., Sympathetic activrivation of pathogenesis of hypertension and progression of organ damage, Hypertension 1999, 34 (4 Pt 2): 724-728.
Marenzi, Giancarlo, M.D. et al., The Prevention of Radiocontrast-Agent-Induced Nephropathy by Hemofiltration, New England Journal of Medicine, Oct. 2, 2003, vol. 349 (14), 2003 Massachusetts Medical Society, pp. 1333-1340.
Market for infusion pumps grows with an aging population, NWL 97-01, The BBI Newsletter, vol. 20, No. 2, Feb. 1, 1997, American Health Consultants, Inc., pp. 6.
Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.
McCreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.
McCullough, Peter A., M.D., MPH et al., Acute Renal Failure after Coronary Intervention: Incidence, Risk Factors and Relationship to Mortality, Apr. 14, 1997, Am J Med. 1997, vol. 103, 1997 Excerpta Medica, Inc., pp. 368-375.
McMurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.
McRobbie, D. and M.A. Foster, Thresholds for biological effects of time-varying magnetic fields, Dec. 16, 1983, Clin. Phys. Physiol. Meas. 1984, vol. 5, No. 2, 1984 The Institute of Physics, pp. 67-78.
Medtronic Neurostimulation Systems, Expanding the Array of Pain Control Solutions, informational pamphlet, 1999 Medtronic, Inc., 6 pages.
Medtronic, Spinal Cord Stimulation, Patient Management Guidelines for Clinicians, Medtronic, Inc. 1999, 115 pages.
Medtronic, SynchroMed Infusion System—Clinical Reference Guide for Pain Therapy, Medtronic, Inc. 1998, 198 pages.
Mehran, Roxana, Renal insufficiency and contrast nephropathy: The most common, least understood risk factor, Cardiovascular Research Foundation, Columbia University Medical Center, 2005, 86 slides.
Mess, Sarah A., M.D. et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.
Micro ETS Hyperhidrosis USA Hyperhidrosis USA. 2 pgs. <URL: http://www.hyperhidrosis-usa.com/Index.html>. Nov. 6, 2006.
Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.
Miklavčič, D. et al, A Validated Model of in Vivo Electric Field Distribution in Tissues for Electrochemotherapy and for DNA Electrotransfer for Gene Therapy, Biochimica et Biophysica Acta, 1523, 2000, pp. 73-83, <http:www.elsevier.com/locate/bba>.
Mitchell, G. A. G., The Nerve Supply of the Kidneys, Aug. 20, 1949, Acta Anatomica, vol. X, Fasc. ½, 1950, pp. 1-37.
Morrisey, D.M. et al., Sympathectomy in the treatment of hypertension: Review of 122 cases, Lancet. 1953;1:403-408.
Moss, Nicholas G., Renal function and renal afferent and efferent nerve activity, Am. J. Physiol. 1982, vol. 243, 1982 the American Physiological Society, pp. F425-F433.
Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.
Naropin (ropivacaine HCI) Injection, RX only Description, AstraZeneca 2001, 3 pages.
National High Blood Pressure Education Program, 1995 Update of the Working Group Reports on Chronic Renal Failure and Renovascular Hypertension, presentation, 13 pages.
National Kidney Foundation, Are You At Increased Risk for Chronic Kidney Disease?, 2002 National Kidney Foundation, Inc., 14 pages.
Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.
Nikolsky, Eugenia, M.D. et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.
Non-Final Office Action; U.S. Appl. No. 10/408,665; Mailed on Mar. 21, 2006, 14 pgs.
Non-Final Office Action; U.S. Appl. No. 11/129,765; Mailed on May 18, 2007, 10 pgs.
Non-Final Office Action; U.S. Appl. No. 11/129,765; Mailed on Sep. 10, 2007, 5 pgs.
Non-Final Office Action; U.S. Appl. No. 11/129,765; Mailed on Oct. 6, 2006, 30 pgs.
Non-Final Office Action; U.S. Appl. No. 11/133,925; Mailed on Oct. 8, 2008, 41 pgs.
Non-Final Office Action; U.S. Appl. No. 11/144,173; Mailed on Apr. 5, 2007, 33 pgs.
Non-Final Office Action; U.S. Appl. No. 11/144,173; Mailed on Sep. 10, 2007, 5 pgs.
Non-Final Office Action; U.S. Appl. No. 11/144,298; Mailed Oct. 29, 2009, 8 pgs.
Non-Final Office Action; U.S. Appl. No. 11/144,298; Mailed on Apr. 5, 2007, 33 pgs.
Non-Final Office Action; U.S. Appl. No. 11/144,298; Mailed on Sep. 10, 2007, 5 pgs.
Non-Final Office Action; U.S. Appl. No. 11/144,298; Mailed on Dec. 29, 2008, 7 pgs.
Non-Final Office Action; U.S. Appl. No. 11/145,122; Mailed on Apr. 11, 2007, 33 pgs.
Non-Final Office Action; U.S. Appl. No. 11/145,122; Mailed on Sep. 10, 2007, 5 pgs.
Non-Final Office Action; U.S. Appl. No. 11/189,563; Mailed on May 28, 2009, 5 pgs.
Non-Final Office Action; U.S. Appl. No. 11/233,814; Mailed on Jun. 17, 2008, 12 pgs.
Non-Final Office Action; U.S. Appl. No. 11/252,462; Mailed on Feb. 22, 2010, 6 pgs.
Non-Final Office Action; U.S. Appl. No. 11/266,993; Mailed on Jul. 8, 2009, 5 pgs.
Non-Final Office Action; U.S. Appl. No. 11/266,993; Mailed on Dec. 30, 2008, 7 pgs.
Non-Final Office Action; U.S. Appl. No. 11/363,867; Mailed on Sep. 25, 2008, 10 pgs.
Non-Final Office Action; U.S. Appl. No. 11/368,553; Mailed on May 18, 2010, 4 pgs.
Non-Final Office Action; U.S. Appl. No. 11/368,553; Mailed on Oct. 7, 2009, 5 pgs.
Non-Final Office Action; U.S. Appl. No. 11/368,809; Mailed on Dec. 3, 2009, 4 pgs.
Non-Final Office Action; U.S. Appl. No. 11/368,949; Mailed on Jun. 11, 2010, 6 pgs.
Non-Final Office Action; U.S. Appl. No. 11/368,971; Mailed on Aug. 24, 2010, 9 pgs.
Non-Final Office Action; U.S. Appl. No. 11/451,728; Mailed on Jun. 12, 2008, 41 pgs.
Non-Final Office Action; U.S. Appl. No. 11/451,728; Mailed on Jul. 2, 2009, 5 pgs.
Non-Final Office Action; U.S. Appl. No. 11/451,728; Mailed on Dec. 28, 2009, 7 pgs.
Non-Final Office Action; U.S. Appl. No. 11/504,117; Mailed on Mar. 31, 2009, 10 pgs.
Non-Final Office Action; U.S. Appl. No. 11/599,649; Mailed on Mar. 30, 2009, 10 pgs.

(56) References Cited

OTHER PUBLICATIONS

Non-Final Office Action; U.S. Appl. No. 11/599,649; Mailed on Jun. 23, 2008, 9 pgs.
Non-Final Office Action; U.S. Appl. No. 11/599,723; Mailed on Jun. 26, 2009, 17 pgs.
Non-Final Office Action; U.S. Appl. No. 11/599,723; Mailed on Oct. 15, 2010, 16 pgs.
Non-Final Office Action; U.S. Appl. No. 11/599,882; Mailed on Jul. 6, 2009, 13 pgs.
Non-Final Office Action; U.S. Appl. No. 11/688,178; Mailed on Jun. 28, 2010, 5 pgs.
Non-Final Office Action; U.S. Appl. No. 11/840,142; Mailed on Apr. 3, 2009, 13 pgs.
Non-Final Office Action; U.S. Appl. No. 12/567,521; Mailed on Sep. 3, 2010, 9 pgs.
Non-Final Office Action; U.S. Appl. No. 12/616,708; Mailed Sep. 16, 2010, 10 pgs.
Non-Final Office Action; U.S. Appl. No. 12/725,375; Mailed on Oct. 12, 2010, 14 pgs.
Nozawa, T.et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.
O'Hagan, K.P. et al., Renal denervation decreases blood pressure in DOCA-treated miniature swine with established hypertension, Am J Hypertens., 1990, 3:62-64.
Onesti, G. et al., Blood pressure regulation in end-stage renal disease and anephric man, Circ Res Suppl., 1975, 36 & 37: 145-152.
Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.
Page, I.H. et al., The Effect of Renal Denervation on the Level of Arterial Blood Pressure and Renal Function in Essential Hypertension. J Clin Invest. 1935;14:27-30.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.
Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.
Pappone, Carlo et al., [2004][759] Pulmonary Vein Denervation Benefits Paroxysmal Atrial Fibrillation Patients after Circumferential Ablation, Abstract only. 1 page, Jan. 5, 2004.
Pappone, Carol and Santinelli, Vincenzo. Multielectrode basket catheter: A new tool for curing atrial fibrillation? Heart Rhythm, vol. 3, Issue 4, pp. 385-386. Apr. 2006.
Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.
Petersson, M. et al., Long-term outcome in relation to renal sympathetic activity in patients with chronic heart failure. Eur Heart J. 2005;26:906-13.
Pettersson, A. et al., Renal interaction between sympathetic activity and ANP in rats with chronic ischaemic heart failure, Nov. 25, 1988, Acta Physiol Scand 1989, 135, pp. 487-492.
PHCL 762 Pharmacology of the Autonomic Nervous System, Chapter 2 and 6.8 in Mosby, http://www.kumc.edu/research/medicine/pharmacology/CAI/phc1762.html, last accessed Aug. 24, 2004, 14 pgs.

Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.
Pliquett, U., Joule heating during solid tissue electroporation, Oct. 22, 2002, Med. Biol. Eng. Comput., 2003, vol. 41, pp. 215-219.
Podhajsky R.J. et al, The Histologic Effects of Pulsed and Continuous Radiofrequency Lesions at 42 C to Rat Dorsal Root Ganglion and Sciatic Nerve, SPINE, vol. 30, No. 9, 2005, Lippincott Williams & Wilkins Inc., pp. 1008-1013.
Pope, Jill. Fixing a Hole: Treating Injury by Repairing Cells. The New York Academy of Sciences. Jul. 6, 2006. 6 pgs.
Popovic, Jennifer R. and Margaret J. Hall, 1999 National Hospital Discharge Survey, Apr. 24, 2001, Advance Data, No. 319, CDC, pp. 1-17 & 20.
Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.
Programmable Infusion System, Pumps and Pump Selection, Medtronic Pain Therapies, Medtronic, Inc. Sep. 5, 2001, 2 pgs.
Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.
Pulmonary Concepts in Critical Care Breath Sounds, http://rnbob.tripod.com/breath.htm, last accessed Aug. 23, 2004, 5 pages.
Pulmonary Function Testing, http://jan.ucc.nau.edu/~daa/lecture/pft.htm, last accessed Aug. 23, 2004, 8 pages.
Purerfellner, Helmut and Martinek, Martin. Pulmonary vein stenosis following catheter ablation of atrial fibrillation. Current Opinion in Cardiology. 20; pp. 484-490. 2005.
Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.
Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.
Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.
Ravalia, A. et al., Tachyphylaxis and epidural anaesthesia, Edgware General Hospital, Correspondence, p. 529, Jun. 1989.
Renal Parenchymal Disease, Ch. 26, 5th Edition Heart Disease, A Textbook of Cardiovascular Medicine vol. 2, Edited by Eugene Braunwald, WB Saunders Company, pp. 824-825 1997.
Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.
Richebe, Philippe, M.D. et al., Immediate Early Genes after Pulsed Radiofrequency Treatment: Neurobiology in Need of Clinical Trials, Oct. 13, 2004, Anesthesiology Jan. 2005, vol. 102, No. 1, 2004 American Society of Anesthesiologists, Inc. Lippincott Williams & Wilkins, Inc., pp. 1-3.
Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.
Rosen, S.M. et al., Relationship of Vascular Reactivity to Plasma Renin Concentration in Patients with Terminal Renal Failure, Proc. Dialysis Transplant Forum 1974, pp. 45-47.
Roth, Bradley J. and Peter J. Basser, A Model of the Stimulation of a Nerve Fiber by Electromagnetic Induction, IEEE Transactions on Biomedical Engineering, vol. 37, No. 6, Jun. 1990, pp. 588-597.
Rudin, Asa, M.D. et al., Postoperative Epidural or Intravenous Analgesia after Major Abdominal or Thoraco-Abdominal Surgery,

(56) References Cited

OTHER PUBLICATIONS

The Journal of the American Society of Anesthesiologists, Inc., Anesthesiology 2001, vol. 95, A-970, 1 page.
Rudnick, Michael R. et al., Contrast-induced nephropathy: How it develops, how to prevent it, Cleveland Clinic Journal of Medicine Jan. 2006, vol. 73, No. 1, pp. 75-87.
Rump, L.C., The Role of Sympathetic Nervous Activity in Chronic Renal Failure, J Clinical Basic Cardiology 2001, vol. 4, pp. 179-182.
Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.
Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.
Sabbah, Hani N., Animal Models for Heart Failure and Device Development, Henry Ford Health System. 24 slides, Oct. 17, 2005.
Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.
Schauerte, P et al., Catheter ablation of cardiac autonomic nerves for prevention of vagal atrial fibrillation, Circulation. 102(22). Nov. 28, 2000. Abstract only. 2 pgs.
Schauerte, P et al., Transvenous parasympathetic nerve stimulation in the inferior vena cava and atrioventricular conduction, Journal of Cardiovascular Electrophysiology. 11(1). Jan. 2000. Abstract only. 2 pgs.
Scheiner, Avram, Ph.D., The design, development and implementation of electrodes used for functional electrical stimulation, Thesis paper, Case Western Reserve University, May 1992, 220 pages.
Scherlag, BJ and Po, S., The intrinsic cardiac nervous system and atrial fibrillation, Current Opinion in Cardiology. 21(1):51-54, Jan. 2006. Abstract only. 2 pgs.
Schlaich, M.P. et al., Relation between cardiac sympathetic activity and hypertensive left ventricular hypertrophy. Circulation. 2003;108:560-5.
Schlaich, M.P. et al., Sympathetic augmentation in hypertension: role of nerve firing, norepinephrine reuptake, and angiotensin neuromodulation, Hypertension, 2004, 43:169-175.
Schmitt, Joseph et al., Intravascular Optical Coherence Tomography—Opening a Window into Coronary Artery Disease, LightLab Imaging, Inc. Business Briefing: European Cardiology 2005.
Schoenbach, Karl H. et al, Intracellular Effect of Ultrashort Electrical Pulses, Dec. 26, 2000, Bioelectromagnetics, vol. 22, 2001, Wiley-Liss, Inc. 2001, pp. 440-448.
Schrier, Robert et al., Cardiac and Renal Effects of Standard Versus Rigorous Blood Pressure Control in Autosomal-Dominant Polycistic Kidney Disease, Mar. 23, 2002, Journal of the American Society of Nephrology, American Society of Nephrology 2002, pp. 1733-1739.
Scremin, Oscar U., M.D., Ph.D. and Daniel P. Holschneider, M.D., 31 & 32 . . . An Implantable Bolus Infusion Pump for the Neurosciences, FRP, Apr. 2005, 3 pages.
Sensorcaine—MPF Spinal Injection, informational document, AstraZeneca 2001, 2 pgs.
Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.
Shannon, J.L. et al., Studies on the innervation of human renal allografts, J Pathol. 1998, vol. 186, pp. 109-115.
Shlipak, M.G. et al., The clinical challenge of cardiorenal syndrome. Circulation. 2004;110:1514-7.
Shupak, Naomi M., Therapeutic Uses of Pulsed Magnetic-Field Exposure: A Review, Radio Science Bulletin Dec. 2003, No. 307, pp. 9-32.
Shu-Qing, Liu et al., Old spinal cord injury treated by pulsed electric stimulation, General Hospital of Beijing Command, Beijing, Dec. 6, 1990, 5 pages (full article in Chinese; abstract on last page).
Siegel, RJ et al., Clinical demonstration that catheter-delivered ultrasound energy reverses arterial vasoconstriction, Journal of the American College of Cardiology. 1992. 20; 732-735. Summary only. 2 pgs.
Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.
Sisken, B.F. et al., 229.17 Influence of Non-Thermal Pulsed Radiofrequency Fields (PRF) on Neurite Outgrowth, Society for Neuroscience, vol. 21, 1995, 2 pages.
Skeie, B. et al., Effect of chronic bupivacaine infusion on seizure threshold to bupivacaine, Dec. 28, 1986, Acta Anaesthesiol Scand 1987, vol. 31, pp. 423-425.
Skopec, M., A Primer on Medical Device Interactions with Magnetic Resonance Imaging Systems, Feb. 4, 1997, CDRH Magnetic Resonance Working Group, U.S. Department of Heatlh and Human Services, Food and Drug Administration, Center for Devices and Radiological Health, Updated May 23, 1997, 17 pages, http://www.fda.gov/cdrh/ode/primerf6.html, (last accessed Jan. 23, 2006).
Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.
Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.
Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.
Sluijter, M.D., Ph.D., Radiofrequency Part 2: Thoracic and Cervical Region, Headache and Facial Pain, various pages from, FlivoPress SA, Meggen (LU), Switzerland, 13 pages 2002.
Sluijter, M.D., Ph.D., The Role of Radiofrequency in Failed Back Surgery Patients, Current Review of Pain 2000, vol. 4, 2000 by Current Science Inc., pp. 49-53.
Smithwick, R.H. et al., Hypertension and associated cardiovascular disease: comparison of male and female mortality rates and their influence on selection of therapy, JAMA, 1956, 160:1023-1033.
Smithwick, R.H. et al., Splanchnicectomy for essential hypertension, Journal Am Med Assn, 1953;152:1501-1504.
Smithwick, R.H., Surgical treatment of hypertension, Am J Med 1948, 4:744-759.
Sobotka, Paul A., Treatment Strategies for Fluid Overload, CHF Patients, CHF Solutions. Transcatheter Cardiovascular Therapeutics 2005. 20 slides.
Solis-Herruzo, J.A. et al., Effects of lumbar sympathetic block on kidney function in cirrhotic patients with hepatorenal syndrome, Journal of Hepatology, 1987; 5: 167-173.
Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.
Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.
Steffen, W. et al., Catheter-delivered high intensity, low frequency ultrasound induces vasodilation in vivo, European Heart Journal. 1994. 15; pp. 369-376.
Steg, PG et al., Pulsed ultraviolet laser irradiation produces endothelium-independent relaxation of vascular smooth muscle, Circulation: Journal of the American Heart Association. 1989. pp. 189-197.
Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.

(56) References Cited

OTHER PUBLICATIONS

Strojek, K. et al., Lowering of microalbuminuria in diabetic patients by a sympathicoplegic agent: novel approach to prevent progression of diabetic nephropathy? J Am Soc Nephrol. 2001;12:602-5.
Summary, Critical Reviews in Biomedical Engineering, vol. 17, Issue 5, 1989, pp. 515-529.
Sung, Duk Hyun, M.D. et al., Phenol Block of Peripheral Nerve Conduction: Titrating for Optimum Effect, Jun. 27, 2000, Arch. Phys. Med. Rehabil. vol. 82, May 2001, pp. 671-676.
Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.
Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.
Tamborero, David et al., Incidence of Pulmonary Vein Stenosis in Patients Submitted to Atrial Fibrillation Ablation: A Comparison of the Selective Segmental Ostial Ablation vs. The Circumferential Pulmonary Veins Ablation, Journal of Intervocational Cardiac Electrophysiology. 14; pp. 41-25. 2005.
Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.
Terashima, Mitsuyasu et al. Feasibility and Safety of a Novel CryoPlasty™ System. Poster. 1 page, Mar. 15, 2002.
Thatipelli et al., CT Angiography of Renal Artery Anatomy for Evaluating Embolic Protection Devices, Journal of Vascular and Interventional Radiology, Jul. 2007, pp. 842-846.
The Antihypertensive and Lipid-Lowering Treatment to Prevent Heart Attack Trial, ALLHAT Research Group, JAMA, 2002, vol. 288, pp. 2981-2997.
Thomas, John R. and Oakley, E. Howard N. Chapter 15: Nonfreezing Cold Injury Medical Aspects of Harsh Environments, vol. 1. pp. 467-490, 2001.
Thompson, Gregory W., et al., Bradycardia Induced by Intravascular Versus Direct Stimulation of the Vagus Nerve, Aug. 24, 1997, The Society of Thoracic Surgeons 1998, pp. 637-642.
Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.
Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.
Trapani, Angelo J. et al., Neurohumoral interactions in conscious dehydrated rabbit, Am. J. Physiol. 254, 1988, the American Physiological Society 1988, pp. R338-R347.
Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.
Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.
Trumble, Dennis R. and James A. MaGovern, Comparison of Dog and Pig Models for Testing Substernal Cardiac Compression Devices, Nov. 2003, ASAIO Journal 2004, pp. 188-192.
Tsai, E., Intrathecal drug delivery for pain indications, technique, results, Pain Lecture presentation, Jun. 8, 2001, 31 pages.
Uematsu, Toshihiko, M.D., Ph.D., F.I.C.A. et al., Extrinsic Innervation of the Canine Superior Vena Cava, Pulmonary, Portal and Renal Veins, Angiology—Journal of Vascular Diseases, Aug. 1984, pp. 486-493.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.
Valente, John F. et al., Laparoscopic renal denervation for intractable ADPKD-related pain, Aug. 24, 2000, Nephrol Dial Transplant 2001, vol. 16, European Renal Association-European Dialysis and Transplant Association, p. 160.
Van Antwerp, Bill and Poonam Gulati, Protein Delivery from Mechanical Devices Challenges and Opportunities, Medtronic presentation, 19 pages, Jul. 2003.
Velazquez, Eric J., An international perspective on heart failure and left ventricular systolic dysfunction complicating myocardial infarction: the VALIANT registry, Aug. 5, 2004, European Heart Journal vol. 25, 2004 Elsevier, pp. 1911-1919.
Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.
Villarreal, Daniel et al., Effects of renal denervation on postprandial sodium excretion in experimental heart failure, Oct. 29, 1993, Am J Physiol 266, 1994, pp. R1599-R1604.
Villarreal, Daniel et al., Neurohumoral modulators and sodium balance in experimental heart failure, Nov. 6, 1992, Am. J. Physiol, vol. 264, 1993, pp. H1187-H1193.
Vonend, O. et al., Moxonidine treatment of hypertensive patients with advanced renal failure. J Hypertens. 2003;21:1709-17.
Wagner, C.D. et al., Very low frequency oscillations in arterial blood pressure after autonomic blockade in conscious dogs, Feb. 5, 1997, Am J Physiol Regul Integr Comp Physiol 1997, vol. 272, 1997 the American Physiological Society, pp. 2034-2039.
Wald, Jan D., Ph.D, et al., Cardiology Update: 2003, Sep. 11, 2003, AG Edwards 2003, 120 pages.
Wang, Xi et al., Alterations of adenylyl cyclase and G proteins in aortocaval shunt-induced heart failure, Jul. 2004, Am J Physiol Heart Circ Physiol vol. 287, 2004 the American Physiological Society, pp. H118-H125.
Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.
Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.
Weiner, Richard L., M.D., Peripheral nerve neurostimulation, Neurosurg. Clin. N. Am. vol. 14, 2003, Elsevier, Inc. 2003, pp. 401-408.
Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.
Whitelaw, G.P., Kinsey, D., Smithwick, R.H., Factors influencing the choice of treatment in essential hypertension: surgical, medical, or a combination of both, Am J Surg, 1964, 107:220-231.
Wilson, D.H. et al., The Effects of Pulsed Electromagnetic Energy on Peripheral Nerve Regeneration, Annals New York Academy of Sciences, Oct. 1974, pp. 575-585.
Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.
Wyss, J. Michael et al., Neuronal control of the kidney: Contribution to hypertension, Apr. 8, 1991, Can. J. Physiol. Pharmacol. 1992;70: 759-770.
Yamaguchi, Jun-ichi, M.D. et al., Prognostic Significance of Serum Creatinine Concentration for In-Hospital Mortality in Patients with Acute Myocardial Infarction Who Underwent Successful Primary Percutaneous Coronary Intervention (from the Heart Institute of

(56) References Cited

OTHER PUBLICATIONS

Japan Acute Myocardial Infarction [HIJAMI] Registry), Feb. 24, 2004, The American Journal of Cardiology vol. 93, Jun. 15, 2004, 2004 by Excerpta Medica, Inc., pp. 1526-1528.

Ye, Richard D., M.D., Ph.D., Pharmacology of the Peripheral Nervous System, E-425 MSB, 6 pages, Jan. 2000.

Ye, S. et al., A limited renal injury may cause a permanent form of neurogenic hypertension. Am J Hypertens. 1998;11:723-8.

Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.

Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.

Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.

Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001. pp. 887-892.

Zanchetti, A. et al., Neural Control of the Kidney—Are There Reno-Renal Reflexes?, Clin. and Exper. Hyper. Theory and Practice, A6 (1&2), 1984, Marcel Dekker, Inc. 1984, pp. 275-286.

Zanchetti, A. et al., Practice Guidelines for Primary Care Physicians: 2003 ESH/ESC Hypertension Guidelines, Journal of Hypertension, vol. 21, No. 10, 2003, pp. 1779-1786.

Zanchetti, A.S., Neural regulation of renin release: Experimental evidence and clinical implications in arterial hypertension, Circulation, 1977, 56(5) 691-698.

Zimmermann, Ulrich, Electrical Breakdown, Electropermeabilization and Electrofusion, Rev. Physiol. Biochem. Pharmacol., vol. 105, Springer-Verlag 1986, pp. 175-256.

Zoccali, C. et al., Plasma norepinephrine predicts survival and incident cardiovascular events in patients with end-stage renal disease. Circulation. 2002;105:1354-9.

Zucker, Irving H. et al., The origin of sympathetic outflow in heart failure: the roles of angiotensin II and nitric oxide, Progress in Biophysics & Molecular Biology, vol. 84, 2004, Elsevier Ltd. 2003, pp. 217-232.

Zundert, Jan Van, M.D. Fipp and Alex Cahana, M.D. DAAPM, Pulsed Radiofrequency in Chronic Pain Management: Looking for the Best Use of Electrical Current, Pain Practice 2005, vol. 5, Issue 2, 2005 World Institute of Pain, pp. 74-76.

\* cited by examiner

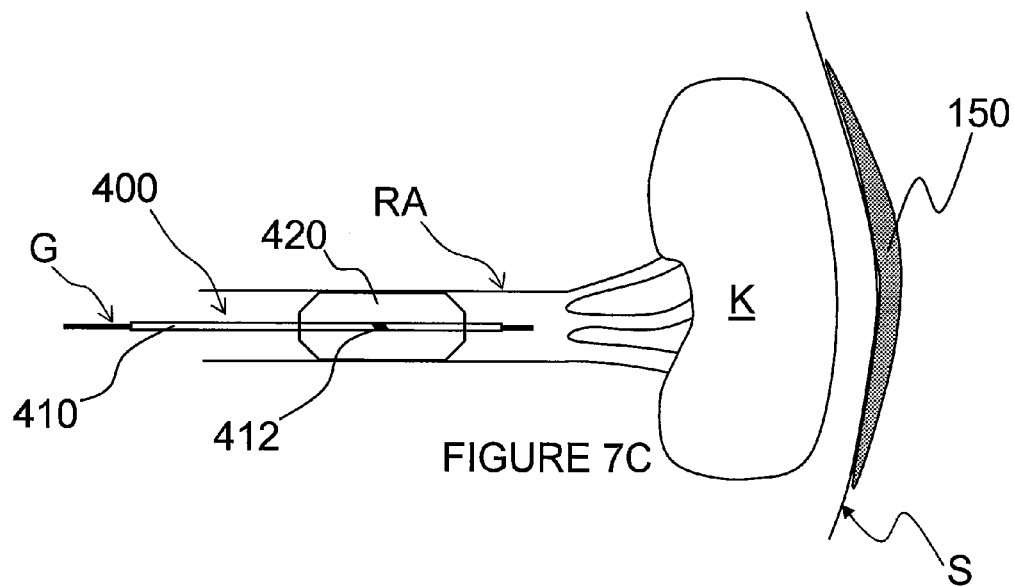
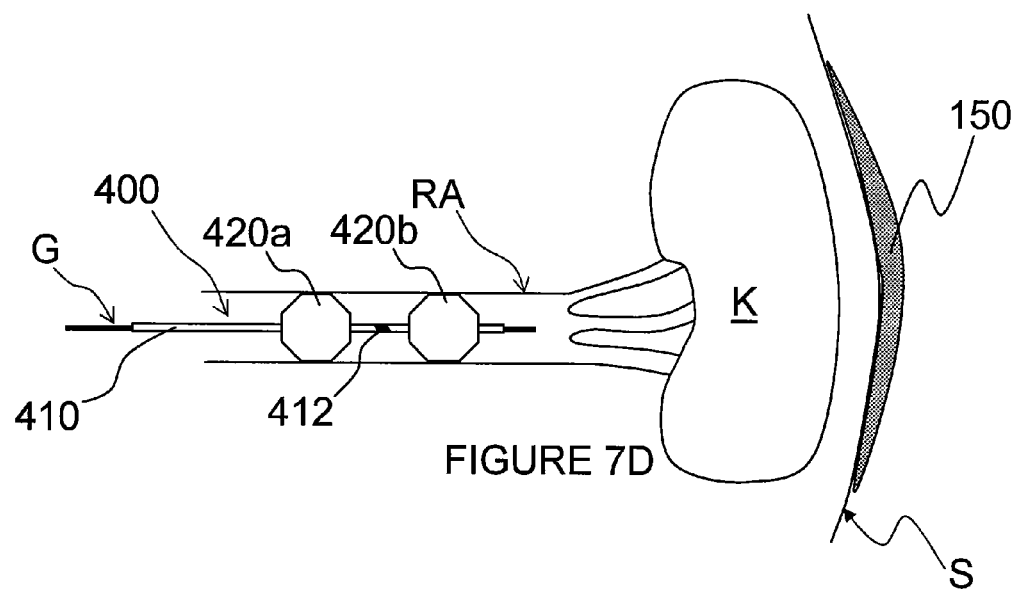

US 9,445,867 B1

METHODS FOR RENAL NEUROMODULATION VIA CATHETERS HAVING EXPANDABLE TREATMENT MEMBERS

REFERENCE TO RELATED APPLICATIONS

The present application is a Continuation of U.S. application Ser. No. 14/611,651, filed Feb. 2, 2015, now allowed, which is a Continuation of U.S. application Ser. No. 13/958,450, filed on Aug. 2, 2013, which is a Continuation of U.S. application Ser. No. 13/371,285, filed on Feb. 10, 2012, which is a Division of U.S. application Ser. No. 11/403,329, filed Apr. 13, 2006, now U.S. Pat. No. 8,131,371, which is a Continuation-In-Part application of the following:

(a) U.S. patent application Ser. No. 11/129,765, filed on May 13, 2005, now U.S. Pat. No. 7,653,438, which claims the benefit of U.S. Provisional Application No. 60/616,254, filed on Oct. 5, 2004; and 60/624,793, filed on Nov. 2, 2004.

(b) U.S. patent application Ser. No. 10/408,665, filed on Apr. 8, 2003, now U.S. Pat. No. 7,162,303, which claims the benefit of U.S. Provisional Patent Application No. 60/442,970, filed on Jan. 29, 2003; 60/415,575, filed on Oct. 3, 2002; and 60/370,190, filed on Apr. 8, 2002.

(c) U.S. patent application Ser. No. 11/189,563, filed on Jul. 25, 2005, now U.S. Pat. No. 8,145,316.

(d) U.S. patent application Ser. No. 11/266,993, filed on Nov. 4, 2005, now U.S. Pat. No. 7,756,583.

(e) U.S. patent application Ser. No. 11/363,867, filed on Feb. 27, 2006, now U.S. Pat. No. 7,620,451, which claims the benefit of U.S. Provisional Application No. 60/813,589, filed on Dec. 29, 2005.

All of these applications, publications and patents are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. In some embodiments, the present invention relates to methods and apparatus for achieving monopolar renal neuromodulation.

BACKGROUND

Congestive Heart Failure ("CHF") is a condition that occurs when the heart becomes damaged and reduces blood flow to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to decreased removal of water and sodium from the body, as well as increased renin secretion. Increased renin secretion leads to vasoconstriction of blood vessels supplying the kidneys which causes decreased renal blood flow. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, Applicants' co-pending U.S. patent application Ser. No. 11/129,765, filed on May 13, 2005, and Ser. No. 11/189,563, filed on Jul. 25, 2005, both of which are incorporated herein by reference in their entireties. A pulsed electric field ("PEF") may initiate renal neuromodulation, e.g., denervation, for example, via irreversible electroporation or via electrofusion. The PEF may be delivered from apparatus positioned intravascularly, extravascularly, intra-to-extravascularly or a combination thereof. Additional methods and apparatus for achieving renal neuromodulation, e.g., via localized drug delivery (such as by a drug pump or infusion catheter) or via use of a stimulation electric field, etc, are described, for example, in co-owned and co-pending U.S. patent application Ser. No. 10/408,665, filed Apr. 8, 2003, and U.S. Pat. No. 6,978,174, both of which are incorporated herein by reference in their entireties.

Electrofusion generally refers to the fusion of neighboring cells induced by exposure to an electric field. Contact between target neighboring cells for the purposes of electrofusion may be achieved in a variety of ways, including, for example, via dielectrophoresis. In tissue, the target cells may already be in contact, thus facilitating electrofusion.

Electroporation and electropermeabilization generally refer to methods of manipulating the cell membrane or intracellular apparatus. For example, the porosity of a cell membrane may be increased by inducing a sufficient voltage across the cell membrane through, e.g., short, high-voltage pulses. The extent of porosity in the cell membrane (e.g., size and number of pores) and the duration of effect (e.g., temporary or permanent) are a function of multiple variables, such as field strength, pulse width, duty cycle, electric field orientation, cell type or size and/or other parameters.

Cell membrane pores will generally close spontaneously upon termination of relatively lower strength electric fields or relatively shorter pulse widths (herein defined as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

A potential challenge of using intravascular PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring tissue impedance or conductivity to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005, which is incorporated herein by reference in its entirety. Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of target and/or non-target tissue may be utilized to determine the onset of electroporation and to determine the type or extent of electroporation. Furthermore, monitoring data may be used in one or more manual or automatic feedback loops to control the electroporation.

In view of the foregoing, it would be desirable to provide additional methods and apparatus for achieving renal neuromodulation.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which:

FIGS. 7A-7D are schematic side views, partially in section, illustrating examples of monopolar intravascular methods and apparatus for renal neuromodulation comprising centering elements.

DETAILED DESCRIPTION

A. Overview

Figure 1:
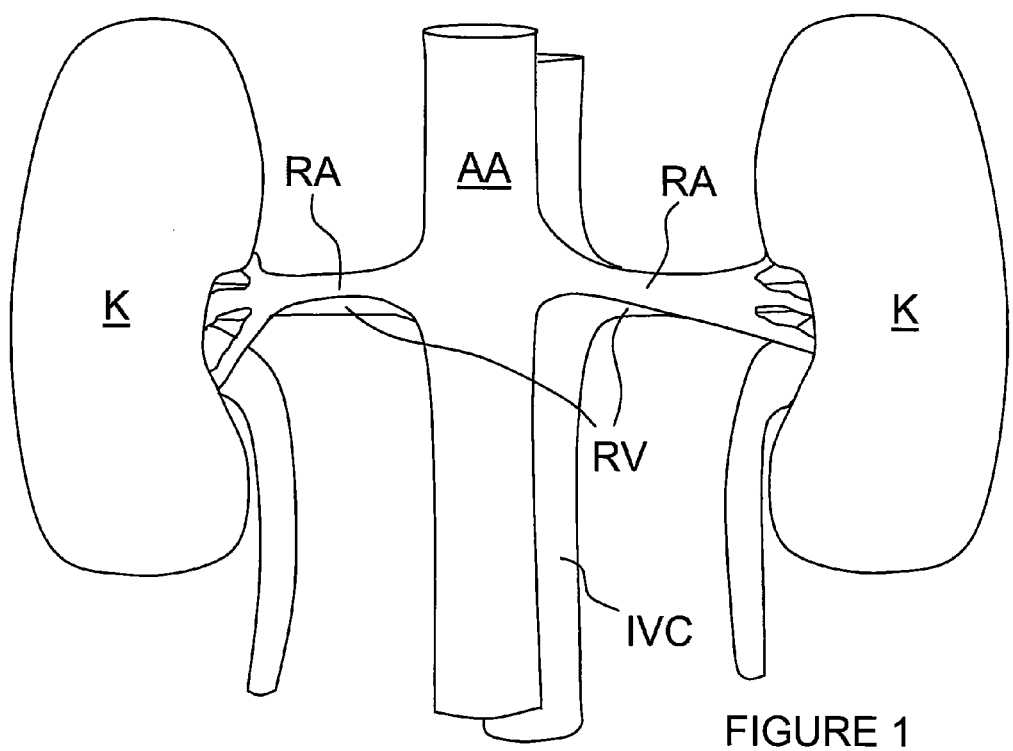
FIG. 1 is a schematic view illustrating human renal anatomy.

Several embodiments of the present invention are methods and apparatus for neuromodulation via a pulsed electric field ("PEF"), a stimulation electric field, localized drug delivery, high frequency ultrasound, thermal techniques, athermal techniques, combinations thereof, and/or other techniques. In some embodiments, neuromodulation is achieved via monopolar (e.g., unipolar) methods and apparatus. Such neuromodulation may, for example, effectuate irreversible electroporation or electrofusion, necrosis and/or inducement of apoptosis, alteration of gene expression, action potential blockade or attenuation, changes in cytokine up-regulation and other conditions in target neural fibers.

In some patients, when the monopolar neuromodulatory methods and apparatus of the present invention are applied to renal nerves and/or other neural fibers that contribute to renal neural functions, applicants believe that the neuromodulatory effects induced by the neuromodulation might result in increased urine output, decreased plasma renin levels, decreased tissue (e.g., kidney) and/or urine catecholamines (e.g., norepinephrine), increased urinary sodium excretion, and/or controlled blood pressure. Furthermore, applicants believe that these or other changes might prevent or treat congestive heart failure, hypertension, acute myocardial infarction, end-stage renal disease, contrast nephropathy, other renal system diseases, and/or other renal or cardio-renal anomalies. The methods and apparatus described herein may be used to modulate efferent or afferent nerve signals, as well as combinations of efferent and afferent nerve signals.

Renal neuromodulation preferably is performed in a bilateral fashion such that neural fibers contributing to renal function of both the right and left kidneys are modulated. Bilateral monopolar renal neuromodulation may provide enhanced therapeutic effect in some patients as compared to renal neuromodulation performed unilaterally, i.e. as compared to renal neuromodulation performed on neural tissue innervating a single kidney. In some embodiments, concurrent modulation of neural fibers that contribute to both right and left renal function may be achieved, or in other embodiments modulation of the right and left neural fibers may be sequential. Bilateral renal neuromodulation may be continuous or intermittent, as desired.

When utilizing an electric field, the electric field parameters may be altered and combined in any suitable combination. Such parameters can include, but are not limited to, voltage, field strength, frequency, pulse width, pulse duration, the shape of the pulse, the number of pulses and/or the interval between pulses (e.g., duty cycle), etc. For example, when utilizing a pulsed electric field, suitable field strengths can be up to about 10,000 V/cm and suitable pulse widths can be up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, or combinations. The field includes at least one pulse, and in many applications the field includes a plurality of pulses. Suitable pulse intervals include, for example, intervals less than about 10 seconds. These parameters are provided as suitable examples and in no way should be considered limiting.

As discussed, the methods and apparatus of the present invention may be used to modulate neural fibers that contribute to renal function and may exploit any suitable neuromodulatory techniques that will achieve the desired neuromodulation. For example, any suitable electrical signal or field parameters, such as any electric field that will achieve the desired neuromodulation (e.g., electroporative effect), may be utilized. In some embodiments, the present invention provides methods and apparatus for achieving bilateral renal neuromodulation. To better understand the structures of devices of the present invention and the methods of using such devices for renal neuromodulation, it is instructive to examine the renal anatomy in humans.

B. Selected Embodiments of Methods for Neuromodulation

Figure 2:
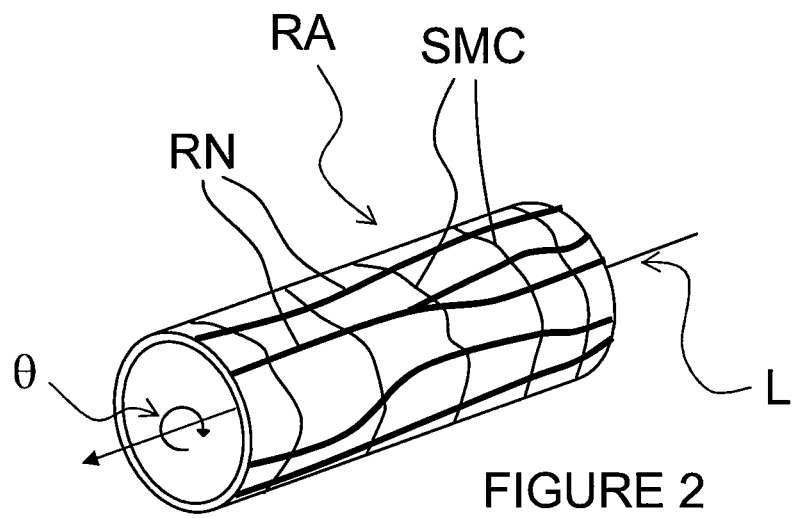
FIG. 2 is a schematic isometric detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
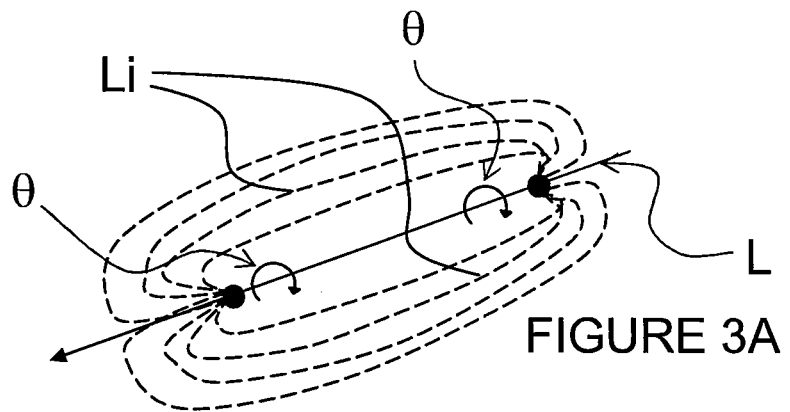
FIGS. 3A and 3B are schematic isometric and end views, respectively, illustrating orienting of an electric field for selectively affecting renal nerves.
Figure 3B:
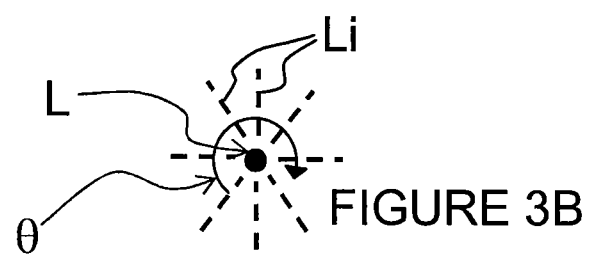

Referring to FIGS. 3A and 3B, the cellular misalignment of the renal nerves and the smooth muscle cells may be exploited to selectively affect renal nerve cells with reduced effect on smooth muscle cells. More specifically, because larger cells require a lower electric field strength to exceed the cell membrane irreversibility threshold voltage or energy for irreversible electroporation, embodiments of the present invention may be configured to align at least a portion of an electric field with or near the longer dimensions of the cells to be affected. In specific embodiments, the device has a monopolar electrode configured to create an electrical field aligned with or near the lengthwise dimension L of the renal artery RA to affect renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells, to induce apoptosis, to alter gene expression, to attenuate or block action potentials, to change cytokine up-regulation and/or to induce other suitable processes. This is expected to reduce total energy delivered to the system and to mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning a pulsed electric field ("PEF") with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIGS. 3A and 3B, applying a PEF with propagation lines Li generally aligned with the longitudinal dimension L of the renal artery RA is expected to preferentially cause electroporation (e.g., irreversible electroporation), electrofusion or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

A PEF system placed within and/or in proximity to the wall of the renal artery may propagate an electric field having a longitudinal portion that is aligned to run with the longitudinal dimension of the artery in the region of the renal nerves RN and the smooth muscle cells SMC of the vessel wall so that the wall of the artery remains at least substantially intact while the outer nerve cells are destroyed, fused or otherwise affected. Monitoring elements optionally may be utilized to assess an extent of, e.g., electroporation, induced in renal nerves and/or in smooth muscle cells, as well as to adjust PEF parameters to achieve a desired effect.

C. Embodiments of Systems and Methods for Neuromodulation

Figure 4:
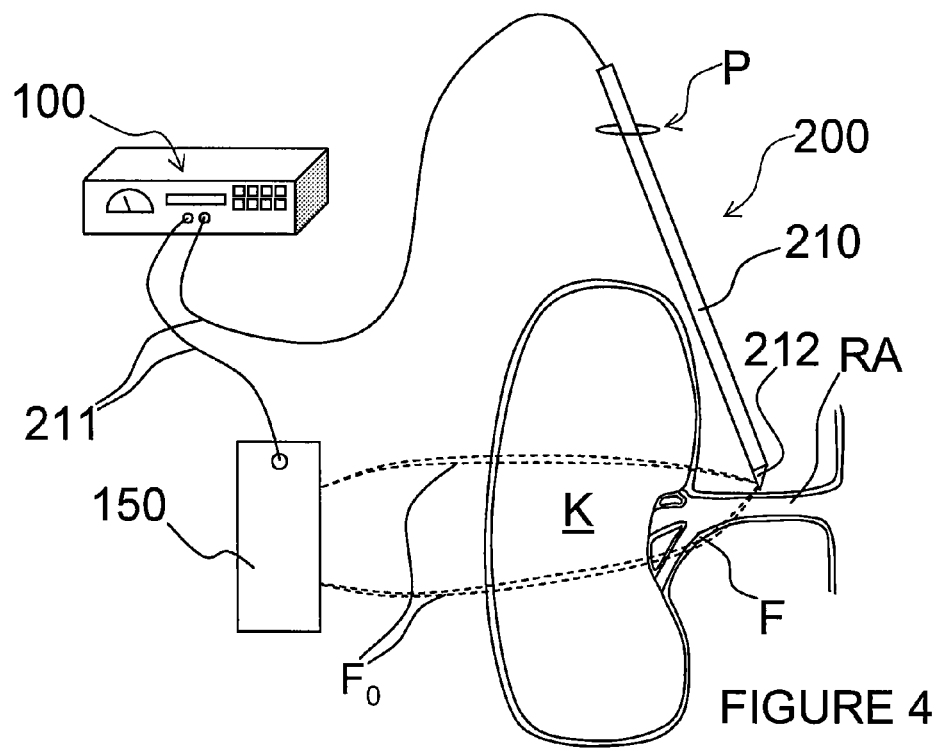
FIG. 4 is a schematic side view, partially in section, illustrating an example of a monopolar extravascular method and apparatus for renal neuromodulation.

With reference to FIGS. 4-10, examples of monopolar PEF systems and methods are described. FIG. 4 shows one embodiment of an extravascular, monopolar pulsed electric field apparatus 200 that includes one or more electrodes configured to deliver a monopolar pulsed electric field to renal neural fibers to achieve renal neuromodulation. The apparatus of FIG. 4 is configured for temporary extravascular placement; however, it should be understood that partially or completely implantable extravascular apparatus additionally or alternatively may be utilized. Applicants have previously described extravascular PEF systems, for example, in co-pending U.S. patent application Ser. No. 11/189,563, filed Jul. 25, 2005, which has been incorporated herein by reference in its entirety.

Apparatus 200 of FIG. 4 comprises a laparoscopic or percutaneous PEF system having a probe 210 configured for insertion in proximity to the track of the renal neural supply. For example, the probe 210 can be configured to be placed along the renal artery or vein, the hilum, and/or within Gerota's fascia under CT, radiographic, ultrasonic, or other suitable guidance. The proximal section of the probe 210 generally has an electrical connector to couple the probe to a pulse generator 100, and the distal section has at least one electrode 212.

The pulsed electric field generator 100 is located external to the patient, and the electrode(s) 212 are electrically coupled to the generator via the probe 210 and wires 211. The generator 100, as well as any of the electrode embodiments described herein, may be utilized with any embodiment of the present invention described hereinafter for delivery of a PEF with desired field parameters. It should be understood that electrodes of embodiments described hereinafter may be electronically connected to the generator even if the generator is not explicitly shown or described with each embodiment.

The electrode(s) 212 can be individual electrodes, a common but segmented electrode, or a common and continuous electrode. A common but segmented electrode may be formed by providing a slotted tube fitted onto the probe, or by electrically connecting a series of individual electrodes. Individual electrodes or groups of electrodes 212 may be configured to provide a monopolar or bipolar signal. The electrodes 212 may be dynamically assignable to facilitate monopolar and/or bipolar energy delivery between/among any of the electrodes on the probe 210 and/or an external ground pad 150. The ground pad 150, for example, may be attached externally to the patient's skin (e.g., to the patient's leg, flank, back or side). Additionally or alternatively, the ground pad 150 may be attached externally to the patient adjacent to the targeted kidney to induce desired directionality in the monopolar electrical field.

As seen in FIG. 4, the electrode 212 may comprise a single electrode that is used in conjunction with a separate ground pad 150 located on the exterior of the patient and coupled to the generator 100 for monopolar use. The probe 210 optionally may comprise a conductive material that is insulated in regions other than its distal tip to form a distal tip electrode 212. Alternatively, the electrode 212 may be delivered through a lumen of the probe 210. The probe 210 and the electrode 212 may be of the standard needle or trocar-type used clinically for pulsed RF nerve block. Alternatively, the apparatus 200 may comprise a flexible and/or custom-designed probe for the renal application described herein.

In FIG. 4, the percutaneous probe 210 has been advanced through a percutaneous access site P into proximity within renal artery RA. Once properly positioned, a pulsed electric field $F_0$ may be applied to target neural fibers across the monopolar electrode 212 and the ground pad 150. The pulsed electric field $F_0$ shown in FIG. 4 is generally aligned with the longitudinal dimension of the neural fibers along the renal artery RA that control the kidney K to preferentially modulate the neural fibers without unduly affecting the smooth muscle cells of the renal artery RA. The monopolar electric field $F_0$, however, can be orientated differently relative to the renal artery RA in other embodiments. After treatment, the apparatus 200 may be removed from the patient to conclude the procedure.

It is expected that applying a monopolar field between the electrode 212 and the ground pad 150 may modulate the function of the target neural fibers in a manner that at least partially denervates the patient's kidney. The neural modulation may be achieved thermally or substantially athermally. Such PEF therapy may alleviate clinical symptoms of CHF, hypertension, renal disease, myocardial infarction, contrast nephropathy and/or other renal or cardio-renal diseases for a period of months (e.g., potentially up to six months or more). This time period may be sufficient to allow the body to heal to potentially reduce the risk of CHF onset after an acute myocardial infarction and mitigate the need for subsequent re-treatment. Alternatively, as symptoms reoccur, or at regularly scheduled intervals, the patient can return to the physician for a repeat therapy.

The effectiveness of the initial therapy, and thus the potential need for repeating the therapy, can be evaluated by monitoring several different physiologic parameters. For example, plasma renin levels, urine catecholamines, or other neurohormones that are indicative of increased sympathetic nervous activity can provide an indication of the extent of denervation. Additionally or alternatively, a nuclear imaging test, such as a test utilizing 131-Iodine metaiodobenzylguanidine ("MIBG"), may be performed to measure a degree of adrenergic innervation. As another option, imaging may be performed with Technetium-99m mercaptoacetylglycine ("Tc-99m MAG3") to evaluate renal function. Alternatively, provocative maneuvers known to increase sympathetic nervous activity, such as head-out water immersion testing, may be conducted to determine the need for repeat therapy.

In some embodiments, the apparatus 200 may comprise a probe having an introducer with an expandable distal segment having one or more electrodes. After insertion in proximity to target neural fibers, the distal segment may be opened or expanded into an expanded configuration. In one embodiment, this expanded configuration would follow a contour of the renal artery and/or vein to treat a number of neural fibers with a single application of PEF therapy. For example, in the expanded configuration, the distal segment may partially or completely encircle the renal artery and/or vein. In another embodiment, the expanded configuration may facilitate mechanical dissection, for example, to expand Gerota's fascia and create a working space for placement of the electrodes and/or for delivery of PEF therapy. The distal segment optionally may be translated independently of the probe or introducer.

When utilized as an electrode, the distal segment may, for example, be extended out of an introducer placed near the treatment area. The conducting distal segment may be advanced out of the sheath until a desired amount of renal neural tissue is in proximity to the distal segment, and then PEF therapy may be delivered via the distal segment electrode. Alternatively, the conducting distal segment may be allowed to reform or expand into a spiral of one or more loops, a random space-occupying shape, or another suitable configuration. Mesh, braid, or conductive gels or liquids could be employed in a similar manner.

Figure 5:
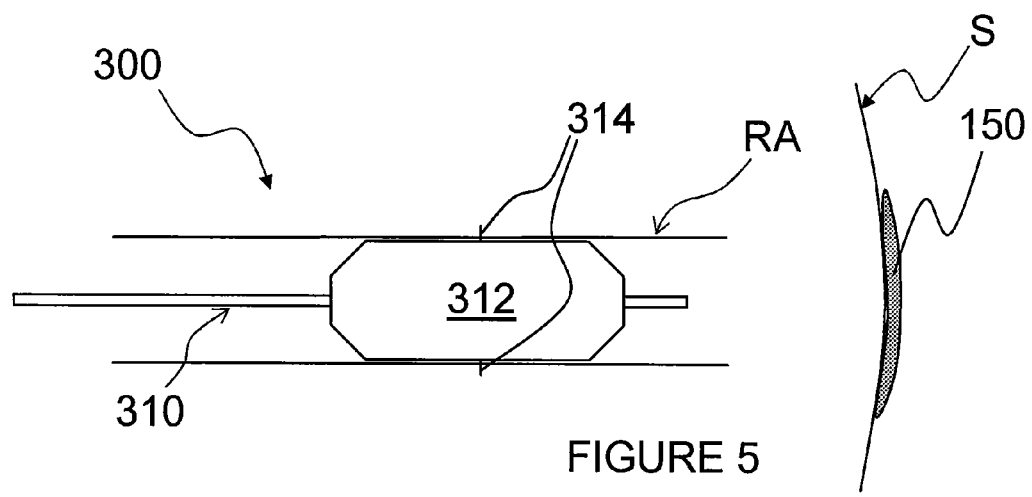
FIG. 5 is a schematic side view, partially in section, illustrating an example of a monopolar intra-to-extravascular method and apparatus for renal neuromodulation.

FIG. 5 schematically illustrates a monopolar intra-to-extravascular (ITEV) PEF system 300 having electrode(s) that are initially delivered endoluminally in a retracted configuration (not shown) to an intravascular position near target neural fibers for modulating renal function. The distal portions of the electrodes then pierce through/across the vessel wall to an extravascular position prior to delivery of the PEF therapy. Intra-to-extravascular positioning of the electrode(s) may place the electrode(s) in closer proximity to target neural fibers during the PEF therapy compared to fully intravascular positioning of the electrode(s). Applicants have previously described intra-to-extravascular PEF systems, for example, in co-pending U.S. patent application Ser. No. 11/324,188, filed Dec. 29, 2005, which is incorporated herein by reference in its entirety.

The example of the monopolar ITEV PEF system 300 shown in FIG. 5 comprises a catheter 310 having an expandable element 312 with one or more needle-like ITEV electrodes 314 coupled to the expandable element. When multiple needle electrodes 314 are provided, they may be spaced circumferentially and/or longitudinally about/along the expandable element 312. The system 300 further comprises the previously described ground pad 150, which may be attached to or otherwise placed against the skin S of the patient along the exterior of the patient (e.g., to the patient's flank, back, thigh or side). The ground pad 150 is also coupled to the PEF generator 100 as a return electrode (see FIG. 4). The ground pad 150 optionally may be positioned substantially directly lateral to the ITEV electrode(s) 314 to direct the PEF therapy along the patient's vasculature (e.g., along renal artery RA).

The expandable element 312 comprises a member or structure configured for intravascular delivery to (and retrieval from) a target location in a low profile configuration and for expansion to an expanded deployed configuration at the target location. The expandable element 312 may comprise, for example, an inflatable balloon, an expandable basket or cage, or some other expandable structure. As seen in FIG. 5, expansion of the expandable element 312 causes the ITEV electrode(s) 314 to pierce the wall of renal artery RA and move from an intravascular location to an extravascular location. With the ITEV electrode(s) 314 positioned extravascularly and coupled to the PEF generator 100, the ITEV electrode(s) may be energized (e.g., one at a time or all together) as active electrodes in a monopolar PEF therapy with the external ground pad 150 serving as the return electrode. Additionally or alternatively, bipolar PEF therapy may be delivered between any pair of the ITEV electrodes 314 in conjunction with or in lieu of monopolar therapy.

Figure 6A:
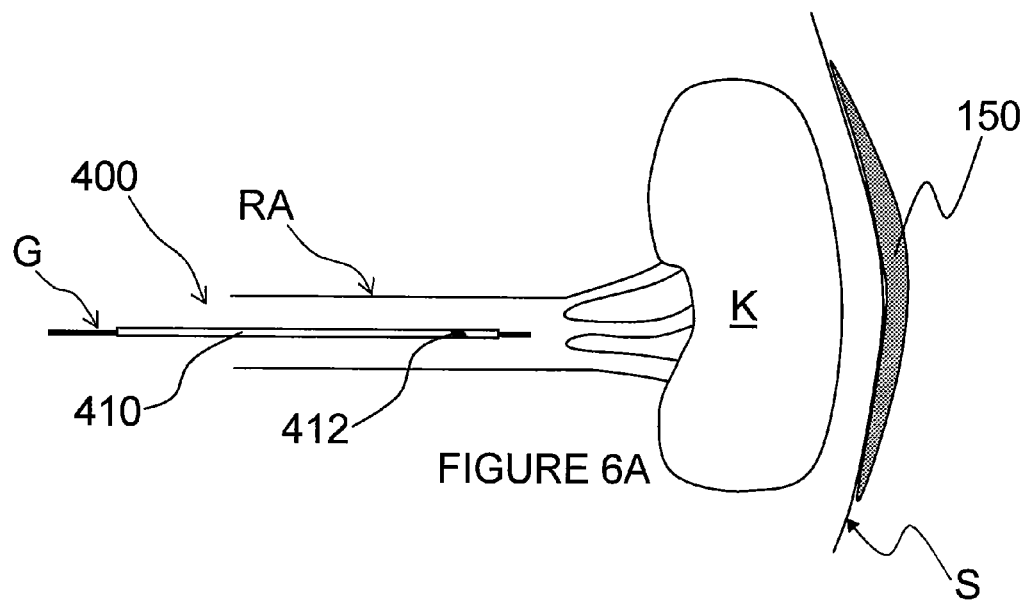
FIGS. 6A and 6B are schematic side views, partially in section, illustrating examples of monopolar intravascular methods and apparatus for renal neuromodulation.
Figure 6B:
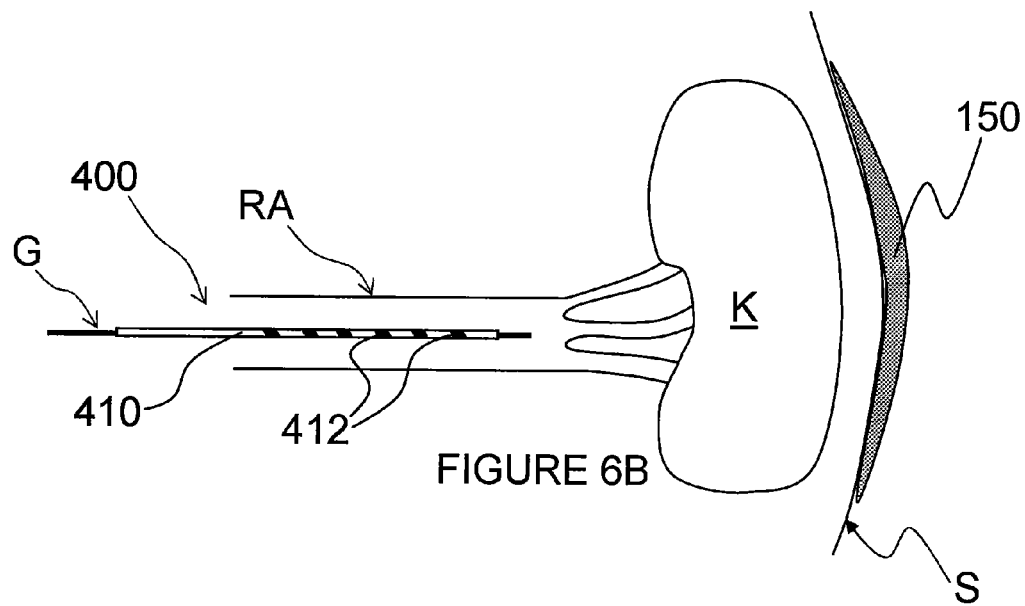

With reference now to FIGS. 6A and 6B, in addition to monopolar extravascular and monopolar ITEV PEF systems, another example of the invention is a monopolar intravascular PEF system 400. Applicants have previously described intravascular PEF systems, for example, in co-pending U.S. patent application Ser. No. 11/129,765, filed May 13, 2005, which has been incorporated herein by reference in its entirety.

The monopolar intravascular PEF system 400 of FIG. 6A comprises a catheter 410 having a monopolar electrode 412 coupled to the shaft of the catheter. The catheter 410 comprises a guide wire lumen for endoluminally advancing the system 400 to a desired intravascular position over a guide wire G (e.g., to a position within a patient's renal artery RA). The electrode 412 may or may not contact the wall of the artery during PEF therapy. The electrode 412 preferably is fabricated from platinum or another material that exhibits relatively high conductivity and radiopacity.

The system 400 further comprises the previously described external ground pad 150, which may be coupled to the PEF generator 100 (FIG. 4) and electrically coupled to the skin S of the patient along the exterior of the patient (e.g., to the patient's flank, back or thigh). As with previous embodiments, the ground pad 150 optionally may be positioned substantially directly lateral to the monopolar electrode 412 to direct the PEF therapy along the patient's vasculature (e.g., the renal artery RA) and/or through the patient's kidney. Such lateral positioning of the ground pad also may provide a relatively uniform distribution of energy about the circumference of the patient's renal artery RA.

FIG. 6B illustrates an alternative embodiment of system 400 comprising a plurality of the electrodes 412 coupled to the shaft of the catheter 410. Providing a plurality of the electrodes may facilitate the monopolar PEF treatment at multiple intravascular locations without necessitating repositioning of the catheter 410. The electrodes may be selectively energized as monopolar (i.e., active) electrodes in any order or combination as desired. In one example, the electrodes may be individually activated in sequence from proximal to distal. In another example, the electrodes may be individually activated in sequence from distal to proximal. In another example, some electrodes are not activated at all. In yet another example, one or more electrodes are activated in combination with one or more other electrodes. In still another example, the electrodes are activated in a pre-determined sequence or in a random sequence. Additional activation protocols will be apparent to those of skill in the art.

In addition or as an alternative to their use in monopolar treatment, the plurality of the electrodes 412 of FIG. 6B optionally may be used for a bipolar PEF treatment. Such a bipolar PEF treatment may be delivered across any pair or pairs of the electrodes 412, as desired. A combination bipolar and monopolar PEF treatment may be more effective than stand-alone bipolar and/or stand-alone monopolar treatment for some patients or for some indications.

Referring to FIGS. 7A-7D, embodiments of the intravascular monopolar PEF system 400 optionally may comprise one or more centering elements for centering the monopolar electrode(s) within the patient's vasculature. The centering element(s) may be partially expanded such that they partially center the monopolar electrode(s) within the vessel, or may be fully expanded as in FIGS. 7A-7D, such that they substantially fully center the electrode(s) within the vessel. The centering elements 420 may, for example, comprise inflatable balloons and/or expandable wire baskets or cages.

The centering element optionally may comprise an impedance-altering element configured to alter impedance within the patient's vasculature to better direct an applied electric field across the vessel wall to target neural fibers. When the centering element is a balloon, it may temporarily block blood flow and thereby alter the impedance within the patient's vessel. Additionally or alternatively, the centering element may comprise the monopolar electrode. In one embodiment, a balloon centering element comprises a conductive exterior and/or is fabricated from a conductive polymer and is used as the monopolar electrode.

Figure 7A:
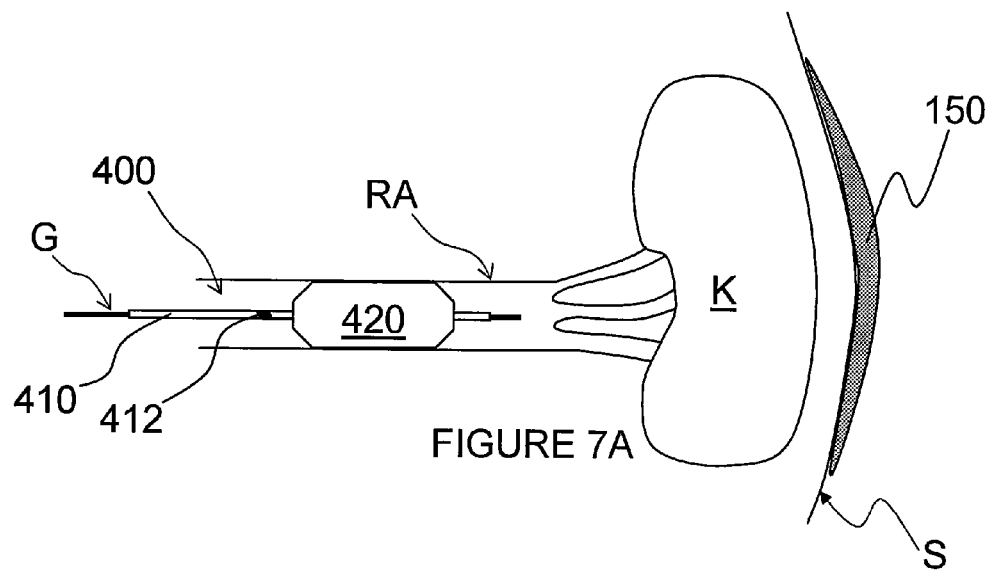

In FIG. 7A, the PEF system 400 comprises an expandable centering element 420 coupled to the catheter 410. The element 420 is configured for delivery and retrieval from a treatment site in a reduced profile delivery configuration, and for expansion at the treatment site to the deployed configuration of FIG. 7A. With the centering element in the fully expanded, deployed configuration of FIG. 7A, the monopolar electrode(s) 412 are substantially centered within the vessel during the PEF therapy.

Figure 7B:
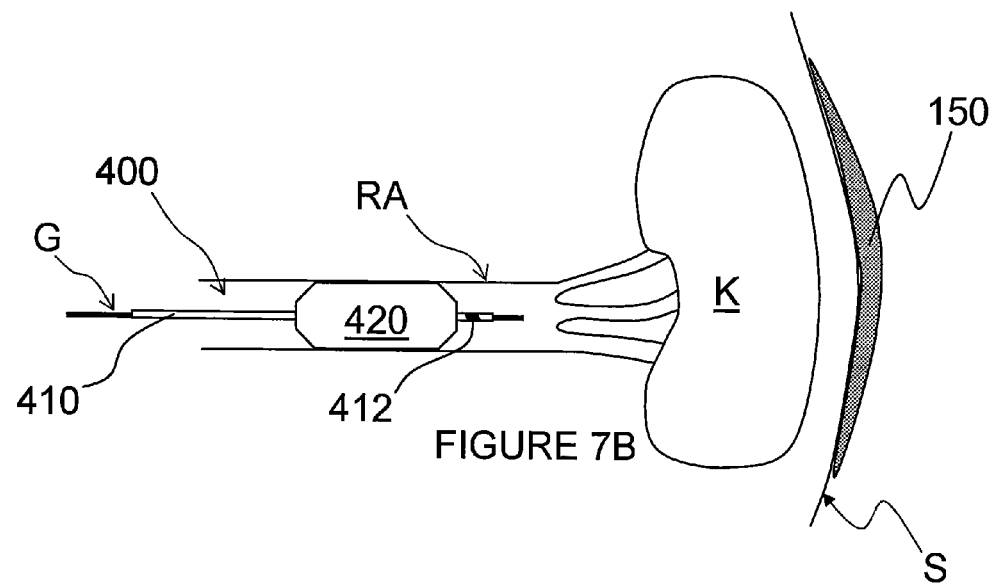

In the embodiment of FIG. 7A, the system 400 comprises a unitary monopolar electrode 412 positioned along the shaft of the catheter 410 proximal of the centering element 420. The centering element is accordingly positioned between the monopolar electrode 412 and the ground pad 150 in this embodiment. In the embodiment of FIG. 7B, the monopolar electrode 412 is positioned distal of the centering element such that the centering element is not positioned between the monopolar electrode and the ground pad. In the embodiment of FIG. 7C, the monopolar electrode 412 is positioned in line with the centering element 420 along the shaft of the catheter 410. In the embodiment of FIG. 7D, the monopolar electrode 412 is positioned between first and second centering elements 420a and 420b, respectively. As will be apparent, additional monopolar and/or bipolar electrodes may be provided with any of the embodiments of the system 400 of FIGS. 7A-7D at any desired position(s) along the catheter 410. Furthermore, one or more electrodes may be coupled to the centering element(s) 420 such that the electrodes contact the wall of the patient's vasculature during delivery of the PEF therapy.

As discussed previously, it is expected that the monopolar PEF therapy, whether delivered extravascularly, intravascularly, intra-to-extravascularly or a combination thereof, may effectuate the following: irreversible electroporation or electrofusion; necrosis and/or inducement of apoptosis; alteration of gene expression; action potential blockade or attenuation; changes in cytokine up-regulation; and other conditions in target neural fibers. In some patients, when such neuromodulatory methods and apparatus are applied to renal nerves and/or other neural fibers that contribute to renal neural functions, applicants believe that the neuromodulatory effects induced by the neuromodulation might result in at least partial denervation of the patient's kidney(s). This may result in increased urine output, decreased plasma renin levels, decreased tissue (e.g., kidney) and/or urine catecholamines (e.g., norepinephrine), increased urinary sodium excretion, and/or controlled blood pressure. Furthermore, applicants believe that these or other changes might prevent or treat congestive heart failure, hypertension, myocardial infarction, renal disease, contrast nephropathy, other renal system diseases, and/or other renal or cardio-renal anomalies for a period of months (e.g., potentially up to six months or more).

The methods and apparatus described herein could be used to modulate efferent or afferent nerve signals, as well as combinations of efferent and afferent nerve signals. Neuromodulation in accordance with the present invention preferably is achieved without completely physically severing, i.e., without fully cutting, the target neural fibers. However, it should be understood that such neuromodulation may functionally sever the neural fibers even though the fibers may not be completely physically severed. Apparatus and methods described herein illustratively are configured for percutaneous use. Such percutaneous use may be endoluminal, laparoscopic, a combination thereof, etc.

The apparatus described herein additionally may be used to quantify the efficacy, extent or cell selectivity of PEF therapy to monitor and/or control the therapy. When a pulsed electric field initiates electroporation, the impedance of the electroporated tissue begins to decrease and the conductivity of the tissue begins to increase. If the electroporation is reversible, the tissue electrical parameters will return or approximate baseline values upon cessation of the PEF. However, if the electroporation is irreversible, the changes in tissue parameters will persist after termination of the PEF. These phenomena may be utilized to monitor both the onset and the effects of PEF therapy. For example, electroporation may be monitored directly using, for example, conductivity measurements or impedance measurements, such as Electrical Impedance Tomography ("EIT") and/or other electrical impedance/conductivity measurements like an electrical impedance or conductivity index. Such electroporation monitoring data optionally may be used in one or more feedback loops to control delivery of PEF therapy.

In order to collect the desired monitoring data, additional monitoring electrodes optionally may be provided in proximity to the monitored tissue. The distance between such monitoring electrodes preferably would be specified prior to therapy delivery and used to determine conductivity from impedance or conductance measurements. For the purposes of the present invention, the imaginary part of impedance may be ignored such that impedance is defined as voltage divided by current, while conductance may be defined as the inverse of impedance (i.e., current divided by voltage), and conductivity may be defined as conductance per unit distance. Applicants have previously described methods and apparatus for monitoring PEF therapy and have provided illustrative PEF waveforms, for example, in co-pending U.S. patent application Ser. No. 11/233,814, filed Sep. 23, 2005, which has been incorporated herein by reference in its entirety.

Figure 8:
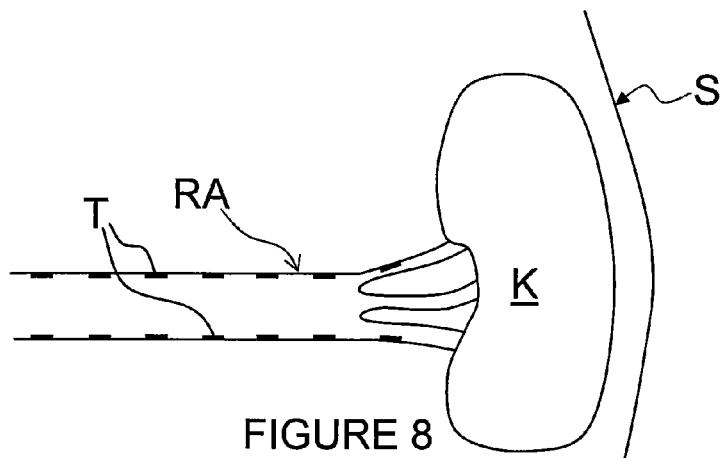
FIG. 8 is a schematic side view, partially in section, illustrating a method for multi-location monopolar renal neuromodulation.

With reference now to FIG. 8, a method for multi-location, monopolar renal neuromodulation is described. In this embodiment, monopolar renal neuromodulation may be performed at a plurality of treatment sites T positioned along the length of renal artery RA. Such multi-location treatment may be achieved utilizing one or more monopolar electrodes positioned intravascularly, intra-to-extravascularly, extravascularly, etc. In FIG. 8, the multi-location treatment is performed with substantially uniform circumferential energy delivery about the renal artery RA. However, it should be understood that non-uniform circumferential energy delivery alternatively may be utilized. For example, in some embodiments the monopolar electrode(s) may contact the vessel wall and may preferentially deliver energy to target neural fibers located in proximity to the contacted side of the wall.

In one embodiment, the catheter 410 of the PEF system 400 of FIG. 6A is repositioned along the renal artery RA for repeat therapy with electrode 412 at multiple locations within the renal artery. In another embodiment, the multiple electrodes 412 of the PEF system 400 of FIG. 6B are utilized to achieve renal neuromodulation at multiple treatment sites T without repositioning the catheter 410. Such multi-location treatment may be achieved, for example, by simultaneously activating multiple electrodes 412 along the length of catheter 410, or by sequentially activating a series of electrodes. All or a subset of the monopolar electrodes of the embodiment of FIG. 6B may be activated to achieve desired renal neuromodulation.

Figure 9:
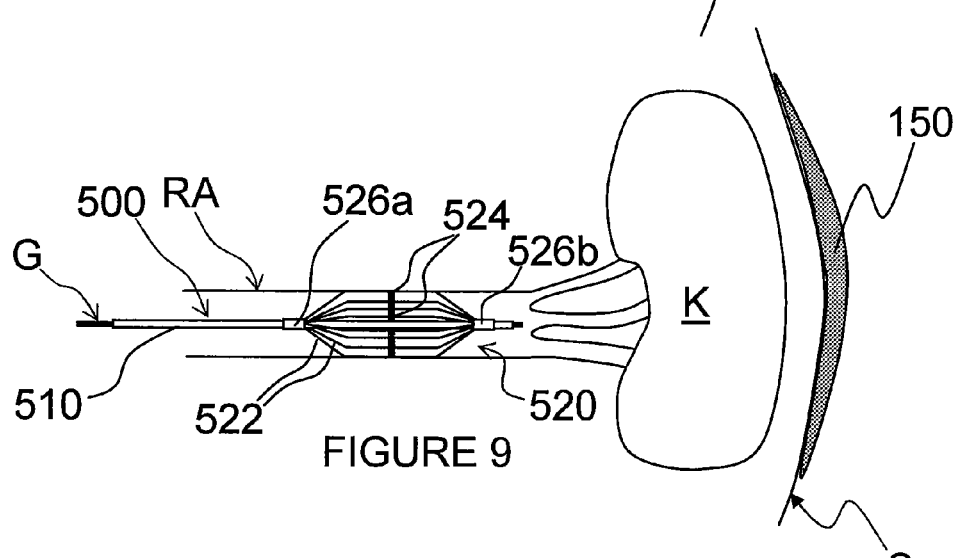
FIG. 9 is a schematic side view, partially in section, illustrating an example of a monopolar intravascular method and apparatus for renal neuromodulation having one or more electrodes that contact the vessel wall.

FIG. 9 schematically illustrates an embodiment of a monopolar PEF system 500 having a plurality of monopolar electrodes that may be expanded into contact with the vessel wall. The PEF system 500 comprises a catheter 510 having an expandable distal cage or basket 520 formed from a plurality of circumferential struts or members. A plurality of electrodes 524 are formed along the members 522 of the basket 520. Each member of the basket illustratively comprises a monopolar electrode configured to contact a wall of the renal artery RA or another desired blood vessel.

The basket 520 may be fabricated, for example, from a plurality of shape-memory wires or ribbons, such as Nitinol, spring steel or elgiloy wires or ribbons, which form the basket members 522. When the basket members comprise ribbons, the ribbons may be moved such that a surface area contacting the vessel wall is increased. The basket members 522 are coupled to the catheter 510 at the proximal and the distal connections 526a and 526b, respectively. In such a configuration, the basket may be collapsed for delivery within a delivery sheath and may self-expand into contact with the wall of the artery upon removal from the sheath. The proximal and/or the distal connection 526 optionally may be configured to translate along the shaft of the catheter 510 for a specified or unspecified distance in order to facilitate the expansion and collapse of the basket.

The basket 520 alternatively may be formed from a slotted and/or a laser-cut hypotube. In such a configuration, the catheter 510 may, for example, comprise an inner and an outer shaft that are moveable relative to one another. The distal connection 526b of the basket 520 may be coupled to the inner shaft, and the proximal connection 526a of the basket may be coupled to the outer shaft. The basket 520 may be expanded from a collapsed delivery configuration to the deployed configuration of FIG. 9 by approximating the inner and the outer shafts of the catheter 510, thereby approximating the proximal and distal connections 526 of the basket and expanding the basket. Likewise, the basket may be collapsed by separating the inner and outer shafts of the catheter.

As seen in FIG. 9, individual electrodes may be arranged along the basket struts or members 522. In one embodiment, the struts are formed from a conductive material coated with a dielectric material, and the electrodes 524 are formed by removing regions of the dielectric coating. The insulation optionally may be removed only along radially outer surfaces of the members such that the electrodes 524 remain insulated on their radially interior surfaces; it is expected that this will direct the current flow outward into the vessel wall.

Other optional fabrication techniques include affixing the electrodes to the inside surfaces and/or outside surfaces of the basket struts, or embedding the electrodes within the struts. The electrode(s) placed along each strut or member may comprise individual electrodes, a common but segmented electrode, or a common and continuous electrode. Individual electrodes or groups of electrodes may be configured to provide a bipolar signal, or all or a subset of the electrodes may be actuated together in conjunction with an external patient ground for monopolar use.

One advantage of having electrodes 524 contact the vessel wall as shown in the embodiment of FIG. 9 is that it may reduce the need for an insulating element, such as an expandable balloon, to achieve renal denervation or other neuromodulation. However, it should be understood that such an insulating element may be provided and, for example, expanded within the basket. Furthermore, having the electrodes contact the wall may provide improved field geometry, i.e., may provide an electric field more aligned with the longitudinal axis of the vessel. Such contacting electrodes also may facilitate stimulation of the renal nerves before, during or after neuromodulation to better position the catheter 510 before treatment or for monitoring the effectiveness of treatment. Furtherstill, wall contact may facilitate multi-location therapy, as in FIG. 8.

Figure 10:
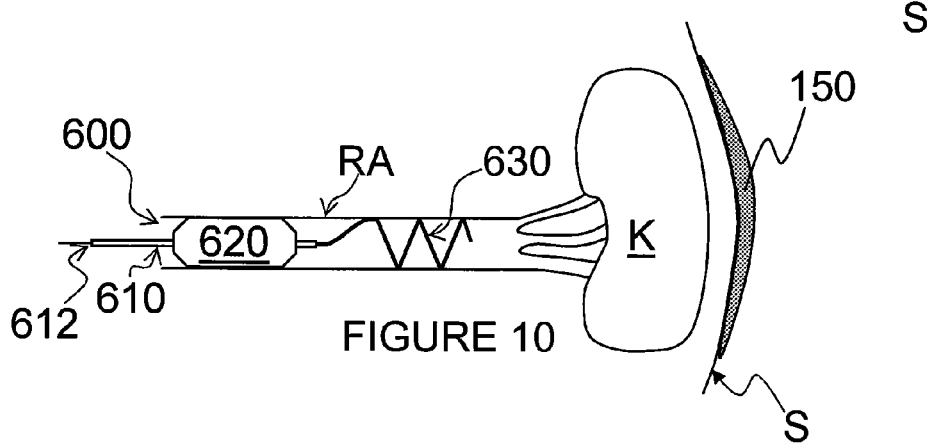
FIG. 10 is a schematic side view, partially in section, illustrating another example of a monopolar intravascular method and apparatus for renal neuromodulation having one or more electrodes that contact the vessel wall

FIG. 10 shows another PEF system 600 having one or more monopolar electrodes that contact the vessel wall. In this embodiment, the PEF system 600 comprises a catheter 610 with an optional expandable centering element 620 (e.g., an optional expandable balloon). The PEF system 600 further comprises an expandable helical electrode 630 configured for delivery in a reduced profile configuration through a guidewire lumen 612 of the catheter 610. The helical electrode 630 may, for example, be fabricated from a self-expanding material, such as Nitinol, elgiloy or spring steel.

As seen in FIG. 10, after positioning the catheter 620 in a target vessel (e.g. renal artery RA), the optional centering element 620 may be expanded, e.g., inflated until it contacts the wall of the vessel to hold the catheter at a desired location within the vessel and/or to insulate or increase the impedance of the interior of the vessel. The helical electrode 630 is pushed through the lumen 612 until the helical electrode extends beyond the catheter shaft; the electrode then expands or otherwise moves into the helical configuration to physically contact the vessel wall. A monopolar pulsed electric field then may be delivered between the helical electrode 630 and external ground pad 150.

Figure 11:
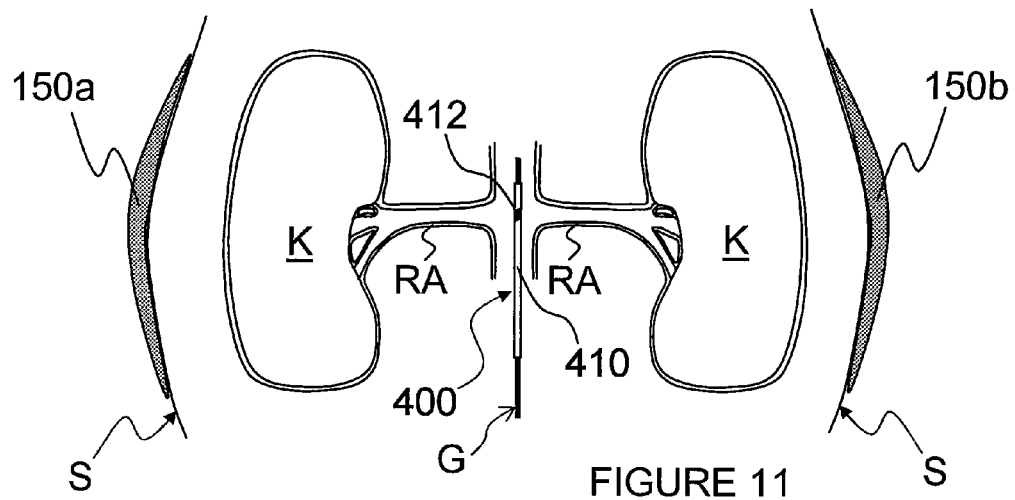
FIG. 11 is a schematic side view, partially in section, of a method for achieving monopolar bilateral renal neuromodulation, illustratively utilizing the apparatus of FIG. 6A.

FIG. 11 illustrates a method for bilateral monopolar renal neuromodulation utilizing the apparatus of FIG. 6A. It should be understood that such bilateral monopolar renal neuromodulation alternatively may be achieved utilizing the extravascular apparatus of FIG. 4 or any other of the foregoing intravascular apparatus, extravascular apparatus, intra-to-extravascular apparatus, or combinations thereof. Bilateral renal neuromodulation may enhance the therapeutic effect in some patients as compared to unilateral renal neuromodulation (i.e., renal neuromodulation performed on neural tissue innervating a single kidney). For example, bilateral renal neuromodulation may further reduce clinical symptoms of CHF, hypertension, myocardial infarction, contrast nephropathy, renal disease and/or other cardio-renal diseases.

As seen in FIG. 11, the catheter 410 of the monopolar PEF system 400 of FIG. 6A may be advanced over a guide wire G into position within the patient's abdominal aorta AA such that the monopolar electrode 412 is substantially in line with the patient's renal arteries RA. First and second ground pads 150a and 150b, respectively, are electrically coupled to the patient's skin S substantially directly lateral to the renal arteries RA. Once the catheter is properly positioned for PEF therapy, the guide wire G may be retracted from the treatment zone (e.g., may be removed from the patient or may be positioned more proximally within the patient's aorta). A pulsed electric field then may be delivered to the active monopolar electrode 412 from the PEF generator 100. The pulsed electric field propagates from the monopolar electrode 412 to the ground pads 150a and 150b to achieve desired bipolar renal neuromodulation.

Monopolar bilateral renal neuromodulation optionally may be performed sequentially by sequentially advancing a monopolar electrode within, or in proximity to, each renal artery RA for PEF therapy. Alternatively, as in the illustrative embodiment FIG. 12, the monopolar electrodes may be positioned simultaneously within both renal arteries RA, but in other embodiments the electrodes can be positioned extravascularly or intra-to-extravascularly with respect to both renal arteries. Monopolar bilateral PEF therapy then may proceed concurrently or sequentially to modulate target neural fibers that contribute to both right and left renal function.

Figure 12:
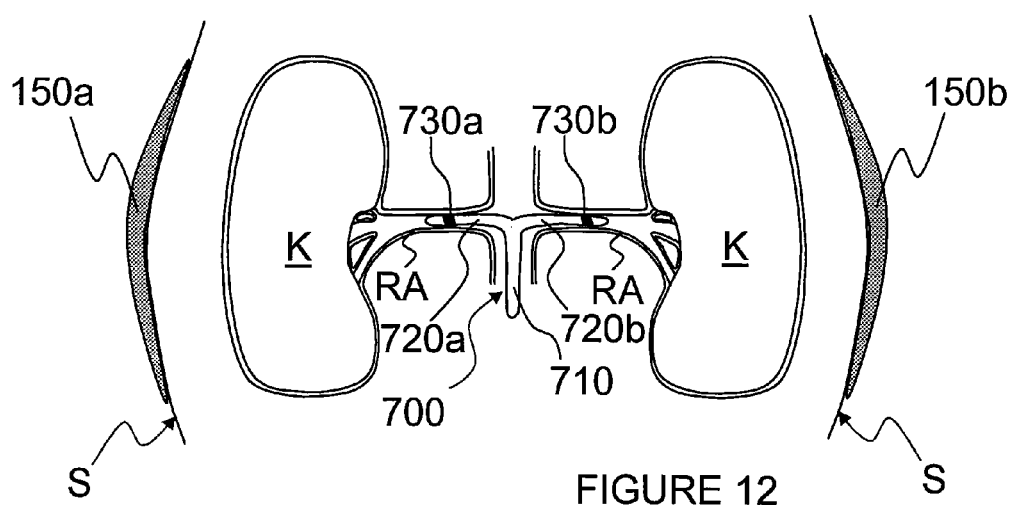
FIG. 12 is a schematic side view, partially in section, illustrating an alternative method and apparatus for achieving monopolar bilateral renal neuromodulation.

FIG. 12 illustrates one embodiment of a bilateral monopolar PEF system 700 that comprises a catheter 710 having a first distal segment 720a with a first monopolar electrode 730a and a second distal segment 720b with a second monopolar electrode 730b. As seen in FIG. 12, the first distal segment 720a may be advanced within a first renal artery RA to position the first monopolar electrode 730a for monopolar therapy in combination with the first ground pad 150a. Likewise, the second distal segment 720b may be advanced within a second renal artery RA to position the second monopolar electrode 730b for monopolar therapy in combination with the second ground pad 150b. As discussed, the bilateral renal neuromodulation may be performed concurrently or sequentially.

Although preferred illustrative variations of the present invention are described above, it will be apparent to those skilled in the art that various changes and modifications may be made thereto without departing from the invention. For example, although the monopolar bilateral methods and apparatus for renal neuromodulation of FIGS. 11 and 12 illustratively utilize dual ground pads, it should be understood that such monopolar bilateral renal neuromodulation alternatively may be performed with a single ground pad. Furthermore, although the illustrative variations described herein generally deliver monopolar renal neuromodulation from within or in proximity to a patient's renal artery, it should be understood that such neuromodulation additionally or alternatively may be delivered from other locations within or in proximity to the patient's renal vasculature, such as within or in proximity to the patient's renal vein. It is intended in the appended claims to cover all such changes and modifications that fall within the true spirit and scope of the invention.

We claim:

1. A method, comprising:
    intravascularly positioning a renal denervation catheter in a reduced profile delivery configuration within a renal artery of a human patient and adjacent to renal nerves;
    transforming an expandable member at a distal region of the catheter from the low-profile delivery configuration to a treatment configuration, wherein, in the treatment configuration, the expandable member is sized and shaped to place a plurality of electrodes arranged thereabout into apposition with an inner wall of the renal artery of the patient;
    selectively energizing a first electrode group carried by the expandable member to deliver a first bipolar energy field to the renal nerves; and
    selectively energizing a second electrode group carried by the expandable member to deliver a second bipolar energy field to the renal nerves,
    wherein delivering the first and second bipolar energy fields blocks or attenuates neural signaling along the renal nerves.

2. The method of claim 1 wherein the expandable member comprises a basket having a plurality of struts, and wherein transforming the expandable member from the low-profile delivery configuration to the treatment configuration comprises expanding the basket such that electrodes arranged along the individual struts are placed into apposition with the inner wall of the renal artery.

3. The method of claim 2 wherein the basket is composed of nitinol.

4. The method of claim 2 wherein the basket comprises a laser-cut hypotube.

5. The method of claim 2 wherein the basket is positioned within the renal artery in the low-profile delivery configuration within a delivery sheath, and wherein the basket is configured to self-expand to the treatment configuration upon removal from the sheath.

6. The method of claim 2 wherein the individual electrodes are affixed to an outside surface of corresponding struts of the basket, and wherein each strut includes at least one electrode.

7. The method of claim 1 wherein the expandable member comprises a balloon, and wherein transforming the expandable member from the low-profile delivery configuration to the treatment configuration comprises expanding the balloon such that electrodes arranged thereabout are placed into contact with the inner wall of the renal artery.

8. The method of claim 7 wherein transforming the balloon from the low-profile delivery configuration to the treatment configuration comprises occluding blood flow within the renal vessel while the balloon is in the treatment configuration.

9. The method of claim 1 wherein blocking or attenuating neural signaling along the renal nerves results in a therapeutically beneficial reduction in blood pressure of the patient.

10. The method of claim 1 wherein selectively energizing the first electrode group and selectively energizing the second electrode group occurs simultaneously.

11. The method of claim 1 wherein selectively energizing the first electrode group and selectively energizing the second electrode group occurs sequentially.

12. The method of claim 1 wherein intravascularly positioning a catheter in a reduced profile delivery configuration within a renal artery of the patient comprises delivering the catheter over a guidewire.

13. The method of claim 1, further comprising monitoring a parameter of the catheter and/or tissue within the patient before and during delivery of the first and second bipolar energy fields.

14. The method of claim 13 wherein monitoring a parameter comprises monitoring temperature, power, and/or impedance.

15. The method of claim 13, further comprising altering delivery of at least one of the first and second bipolar energy fields in response to the monitored parameter.

16. The method of claim 13 wherein monitoring a parameter comprises monitoring temperature of the tissue, and wherein the method further comprises maintaining the tissue at a desired temperature during delivery of the first and second bipolar energy fields.

17. The method of claim 1 wherein delivering the first and second bipolar energy fields to the renal nerves comprises partially ablating the renal nerves of the patient.

18. The method of claim 1 wherein delivering the first and second bipolar energy fields to the renal nerves comprises ablating one or more renal nerves of the patient.

19. The method of claim 1 wherein delivering the first and second bipolar energy fields to the renal nerves comprises thermally altering the renal nerves in a manner that reduces neural traffic to and from a kidney of the patient.

20. A method for treating a hypertensive human patient, the method comprising:
    positioning an expandable member of a renal denervation catheter at an intravascular location within a renal artery of a human patient and adjacent to neural fibers innervating a kidney of the patient;
    transforming the expandable member from a low-profile delivery state to an expanded treatment state wherein, in the treatment state, the expandable member is sized to place a first set of electrodes carried by a first region of the expandable member and a second set of electrodes carried by a second, different region of the expandable member in contact with target tissue at or near the neural fibers; and
    ablating the neural fibers innervating the kidney via radio frequency (RF) energy delivered from the first and second sets of electrodes.

21. The method of claim 20 wherein positioning an expandable member of a renal denervation catheter within a renal artery comprises positioning an expandable basket carrying the first and second sets of electrodes within the renal artery.

22. The method of claim 20 wherein positioning an expandable member of a renal denervation catheter within a renal artery comprises positioning a balloon carrying the first and second sets of electrodes within the renal artery.

23. The method of claim 20 wherein ablating the neural fibers innervating the kidney results in a therapeutically beneficial reduction in blood pressure of the patient.

24. The method of claim 20, further comprising monitoring a parameter of the renal denervation catheter and/or tissue within the patient before and during delivery of the RF energy.

25. The method of claim 24 wherein monitoring a parameter comprises monitoring temperature, power, and/or impedance, and wherein the method further comprises altering delivery or the RF energy in response to the monitored parameter.

* * * * *